(12) United States Patent
Centanni et al.

(10) Patent No.: US 11,041,186 B2
(45) Date of Patent: Jun. 22, 2021

(54) CAPACITOR FOR DETECTING VIABLE MICROORGANISMS

(71) Applicant: American Sterilizer Company, Mentor, OH (US)

(72) Inventors: Michael A. Centanni, Parma, OH (US); Phillip P. Franciskovich, Concord, OH (US); Kathleen A. Fix, Willoughby, OH (US)

(73) Assignee: American Sterilizer Company, Mentor, OH (US)

(*) Notice: Subject to any disclaimer, the term of this patent is extended or adjusted under 35 U.S.C. 154(b) by 67 days.

(21) Appl. No.: 15/375,256

(22) Filed: Dec. 12, 2016

(65) Prior Publication Data
US 2017/0211122 A1 Jul. 27, 2017

Related U.S. Application Data

(60) Provisional application No. 62/425,745, filed on Nov. 23, 2016, provisional application No. 62/286,621, filed on Jan. 25, 2016.

(51) Int. Cl.
| | | |
|---|---|---|
| *C12M 3/00* | (2006.01) | |
| *C12Q 1/00* | (2006.01) | |
| *C12Q 1/22* | (2006.01) | |
| *A61L 2/28* | (2006.01) | |
| *C12M 1/34* | (2006.01) | |
| *G01N 27/22* | (2006.01) | |

(52) U.S. Cl.
CPC ............. *C12Q 1/22* (2013.01); *A61L 2/28* (2013.01); *C12M 1/3407* (2013.01); *C12M 41/46* (2013.01); *G01N 27/221* (2013.01)

(58) Field of Classification Search
CPC ................................. C12M 37/06; C12Q 1/22
See application file for complete search history.

(56) References Cited

U.S. PATENT DOCUMENTS

| | | | |
|---|---|---|---|
| 5,552,320 A * | 9/1996 | Smith | A61L 2/28 422/28 |
| 5,736,355 A | 4/1998 | Dyke et al. | |
| 6,132,683 A * | 10/2000 | Sugihara | G01N 33/4836 204/403.01 |

(Continued)

FOREIGN PATENT DOCUMENTS

| | | |
|---|---|---|
| WO | WO 02/14490 | 2/2002 |
| WO | WO 2008/079469 | 7/2008 |

OTHER PUBLICATIONS

Oberlander et al.; "Study of Interdigitated Electrode Arrays Using Experiments and Finite Element Models for the Evaluation of Sterilization Processes"; *Sensors* 2015, 15, 26115-26127.

(Continued)

*Primary Examiner* — Nathan A Bowers
(74) *Attorney, Agent, or Firm* — Renner, Otto, Boisselle & Sklar, LLP

(57) ABSTRACT

This invention relates to a capacitor comprising two electrical conductors separated by a dielectric, the dielectric comprising microorganisms. The dielectric may comprise a biological indicator. This invention relates to a process for determining whether the microorganisms are alive or dead. The number of microorganisms can be determined. This invention relates to a process for testing the efficacy of a sterilization process using the capacitor.

5 Claims, 7 Drawing Sheets

(56) References Cited

U.S. PATENT DOCUMENTS

| | | | |
|---|---|---|---|
| 6,280,586 B1* | 8/2001 | Wolf | G01N 33/54373 204/403.01 |
| 6,844,742 B2 | 1/2005 | Centanni | |
| 6,897,661 B2 | 5/2005 | Allen et al. | |
| 6,909,972 B2 | 6/2005 | Centanni | |
| 6,917,885 B2 | 7/2005 | Centanni | |
| 6,927,582 B2 | 8/2005 | Kaiser et al. | |
| 6,930,493 B2 | 8/2005 | Kaiser et al. | |
| 6,933,733 B2 | 8/2005 | Korenev et al. | |
| 6,946,852 B2 | 9/2005 | Centanni | |
| 6,960,921 B2 | 11/2005 | Kaiser et al. | |
| 6,992,494 B2 | 1/2006 | Kaiser | |
| 7,431,886 B2 | 10/2008 | Centanni | |
| 7,527,766 B2 | 5/2009 | Centanni | |
| 7,541,002 B2 | 6/2009 | Centanni | |
| 7,611,667 B2 | 11/2009 | Centanni | |
| 7,901,618 B2 | 3/2011 | Centanni | |
| 7,955,560 B2 | 6/2011 | Centanni | |
| 8,343,768 B2* | 1/2013 | Kyung-Hee Song | A61L 2/28 422/28 |
| 8,372,624 B2 | 2/2013 | Franciskovich et al. | |
| 8,507,248 B2 | 8/2013 | Franciskovich et al. | |
| 8,815,574 B2 | 8/2014 | Bachur, Jr. et al. | |
| 8,945,837 B2 | 2/2015 | Franciskovich et al. | |
| 8,969,029 B2* | 3/2015 | Chandrapati | C12Q 1/22 435/31 |
| 9,362,980 B2 | 6/2016 | Han et al. | |
| 9,400,272 B2 | 7/2016 | Bachur, Jr. et al. | |
| 2002/0028480 A1* | 3/2002 | Maher | G01N 33/5008 435/40 |
| 2006/0087522 A1* | 4/2006 | Muller-Hartmann | B01J 19/0046 347/1 |
| 2007/0003995 A1 | 1/2007 | Song et al. | |
| 2008/0070231 A1 | 3/2008 | Franciskovich et al. | |
| 2008/0070272 A1 | 3/2008 | Franciskovich et al. | |
| 2009/0047176 A1 | 2/2009 | Cregger | |
| 2009/0117603 A1 | 5/2009 | Franciskovich et al. | |
| 2010/0248296 A1 | 9/2010 | Franciskovich et al. | |
| 2010/0267044 A1 | 10/2010 | Franciskovich et al. | |
| 2012/0021406 A1 | 1/2012 | Franciskovich et al. | |
| 2012/0196355 A1 | 8/2012 | Franciskovich et al. | |
| 2012/0214154 A1 | 8/2012 | Franciskovich et al. | |
| 2012/0293189 A1 | 11/2012 | Qureshi et al. | |
| 2013/0089922 A1 | 4/2013 | Franciskovich et al. | |
| 2013/0199955 A1 | 8/2013 | Franciskovich et al. | |
| 2013/0217001 A1 | 8/2013 | Franciskovich et al. | |
| 2013/0217107 A1 | 8/2013 | Pederson et al. | |
| 2013/0224849 A1 | 8/2013 | Chandrapati et al. | |
| 2013/0273594 A1 | 10/2013 | Ahimon et al. | |
| 2014/0162307 A1 | 6/2014 | Franciskovich et al. | |
| 2014/0262829 A1 | 9/2014 | Franciskovich et al. | |
| 2014/0273054 A1 | 9/2014 | Franciskovich et al. | |
| 2014/0273072 A1 | 9/2014 | Franciskovich et al. | |
| 2014/0273073 A1 | 9/2014 | Franciskovich et al. | |
| 2015/0042364 A1 | 2/2015 | Bachur, Jr. et al. | |
| 2015/0147773 A1 | 5/2015 | Franciskovich et al. | |
| 2015/0233852 A1 | 8/2015 | Bommarito et al. | |
| 2017/0247742 A1* | 8/2017 | Doyle | G01N 31/222 |

OTHER PUBLICATIONS

Terzic et al.; "Capacitive Sensing Technology"; *A Neural Network to Fluid Quantity Measurement in Dynamic Environments*; Jan. 1, 2012; pp. 11-37.

Baxter; "Capacitive Sensors"; Jul. 20, 2000; Retrieved from Internet: URL:http://www.capsense.com/capsense-wp.pd.

Horta et al.; "On-Line Monitoring of Biomass Concentration Based on a Capacitance Sensor: Assessing the Methodology for Different Bacteria and yeast High Cell Density Fed-Batch Cultures"; *Brazilian Journal of Chemical Engineering*; vol. 32, No. 4, Dec. 1, 2015; pp. 821-829.

Anonymous: "Calibration curve—Wikipedia"; Jan. 6, 2016; Retrieved from Internet: URL:https://en.wikipedia.org/w/index.php?t.

Anonymous; "One Point Calibration Calibrating Sensors; Adafruit Learning System"; May 18, 2015; Retrieved from Internet: URL:https://learn.adafruit.com/calibrating-sensors/single-point-calibrating.

International Search Report and Written Opinion of the International Searching Authority; Application No. PCT/US2016/066104; dated Aug. 11, 2017.

Albert et al.; "Biological indicators for steam sterilization: characterization of a rapid biological indicator utilizing Bacillus stearothermophilus spore-associated alpha-glucosidase enzyme"; Journal of Applied Microbiology; 1998; pp. 865-874.

Mahillon et al.; Microbiology and Molecular Biology Reviews, Sep. 1998, p. 725-774; vol. 62, No. 3.

Kohman; "Cellulose as an Insulating Material"; Industrial and Engineering Chemistry; vol. 31, No. 7; pp. 807 and 810; date unknown but Applicants admit it is prior art.

Dwivedi; et al.; Detection of *E. coli* Cell Using Capacitance Modulation; Excerpt from the Proceedings of the COMSOL Conference, 2010.

Ah Andeen-Hagerling; product brochure for AH2700A 50 Hz-20kHz Ultra-precision Capacitance Bridge; 2010.

Mirus Bio, LLC; product brochure for Ingenio® Electroporation Kits and Solution; 2014; 2014.

Bio-Rad, Products for Life Science Research & Clinical Diagnostics; http://www.bio-rad.com; 2 pages; Oct. 25, 2016.

Keysight Technologies U1701B Handheld Capacitance Meter product description and information; www.2daydeliver.com/product_detail.php? . . . .; Oct. 25, 2016.

Bio-Rad, Instruction Manual for Gene Pulser MCcell™ ShockPod™ Cuvette Chamber; date unknown but Applicants admit it is prior art.

STERIS Safety Data Sheet for Verify® Spore Test Strip for S40™ Sterilant; 2016.

Preliminary; Notes and Guidelines for Designing Test Fixtures and Test Environments for High Precision Capacitance Measurements with AH Bridges; date unknown but Applicants admit it is prior art.

* cited by examiner

CAPACITOR FOR DETECTING VIABLE MICROORGANISMS

This application claims priority under 35 U.S.C. § 119(e) to U.S. Provisional Application Ser. No. 62/286,621, filed Jan. 25, 2016, and to U.S. Provisional Application Ser. No. 62/425,745, filed Nov. 23, 2016. These applications are incorporated herein by reference.

TECHNICAL FIELD

This invention relates to a capacitor for detecting viable microorganisms. The capacitor may comprise electrical conductors and a dielectric. The dielectric may comprise a biological indicator and an assay medium. The capacitor may be used for evaluating the efficacy of a sterilization process and for counting microorganisms.

BACKGROUND

Biological indicators, which typically comprise test microorganisms (e.g., spores), are used for evaluating the efficacy of sterilization processes. The biological indicator is placed in a sterilization chamber and subjected to a sterilization process along with the load intended for sterilization (e.g., a medical device). Following the sterilization process, the biological indicator is exposed to a growth media and incubated for the purpose of determining if any of the test microorganisms are viable. A successful sterilization process is indicated by a complete inactivation (no outgrowth) of the test microorganisms. An unsuccessful sterilization process is indicated by an incomplete inactivation (outgrowth detected) of the test microorganisms.

SUMMARY OF THE INVENTION

Primarily in the health care industry, but also in many other commercial and industrial applications, it is often necessary to monitor the effectiveness of the processes used to sterilize equipment such as medical and non-medical devices, instruments and other articles and materials. It is often standard practice in these sterilization processes to include a biological indicator in the batch of articles to be sterilized. This allows a direct approach to assay the lethality of the sterilization process.

Methods of sterility assurance typically involve exposing a biological indicator containing test microorganisms to the sterilization process and then measuring the outgrowth of any surviving test microorganisms. Sterility may be assured if there is no outgrowth of the test microorganisms following exposure to the sterilization process. Bacterial spores (e.g., *Geobacillus stearothermophilus*, *Bacillus atrophaeus*, and the like) may be used as the test microorganisms. Upon completion of the sterilization process, the biological indicator is exposed to a growth medium under conditions that would promote the growth of any surviving test microorganisms. The growth medium often contains a chemical dye which changes color in response to actively growing (metabolizing) cells. Because of the requirement for growth and metabolism, the processes employing these test microorganisms typically require about 24 to 72 hours of incubation before the effectiveness of the sterilization process can be determined. A problem with this process relates to the fact that many users of sterilized articles, such as health care facilities and the like, have limited resources and may reuse the "sterilized" articles within 24 to 72 hours and sometimes immediately. In such settings, the 24 to 72 hour holding period for sterility verification may be impractical, costly and inefficient.

Thus, a problem in the art relates to determining the efficacy of a sterilization process within a short period of time. This invention provides a solution to this problem. With this invention, the efficacy of a sterilization process can be determined instantaneously, or within a period of time of up to about 2000 seconds, or up to about 1500 seconds, or up to about 1000 seconds, or up to about 500 seconds, or up to about 200 seconds, or up to about 100 seconds, or up to about 50 seconds, or up to about 30 seconds, or in the range from about 5 to about 2000 seconds, or from about 10 to about 1800 seconds, or from about 20 to about 1500 seconds, or from about 30 to about 1200 seconds, or from about 50 to about 1000 seconds, or from about 60 to about 800 seconds.

This invention relates to a capacitor comprising two electrical conductors separated by a dielectric, the dielectric comprising a biological indicator and an assay medium, the biological indicator comprising test microorganisms. In an embodiment, the test microorganisms comprise bacteria. In an embodiment, the test microorganisms comprise spores. In an embodiment, the test microorganisms comprise bacterial spores. In an embodiment, the biological indicator comprises spores on a carrier. In an embodiment, the biological indicator comprises bacterial spores on a carrier. In an embodiment, the electrical conductors comprise metal plates or metal sheets. In an embodiment, the capacitor is rolled to form a cylinder with an insulating layer positioned between the electrical conductors. In an embodiment, electric leads are connected to the electrical conductors. In an embodiment, the capacitor is connected to a capacitance bridge. The capacitance bridge may have an accuracy level of about 1 μF or less. In an embodiment, the dielectric has a capacitance in the range from about 0.1 nF to about 20 mF, or about 1 to about 5000 nF. In an embodiment, the dielectric comprises from about 500,000 to about 4,000,000 colony forming units of the test microorganisms. In an embodiment, the dielectric comprises spores, the spores being on a carrier, the spore population on the carrier being in the range from about 500,000 to about 4,000,000 spores. In an embodiment, the test microorganisms are on a carrier, the carrier comprising paper, plastic, glass, ceramics, metal foil, one or both conductors of the capacitor, or a combination of two or more thereof. In an embodiment, each electrical conductor has a length in the range from about 1 to about 5 cm, a width in the range from about 0.5 to about 3 cm. In an embodiment, the electrical conductors are separated by a gap, the separation provided by the gap being in the range from about 0.5 to about 5 mm. In an embodiment, the dielectric comprises a liquid.

This invention relates to a capacitance device, comprising: a first compartment containing a biological indicator, the biological indicator comprising test microorganisms, the first compartment containing two electrical conductors separated by a gap, the biological indicator being positioned in the gap between the electrical conductors, the first compartment being adapted to permit a sterilant to be brought into contact with the biological indicator during a sterilization process; and a second compartment containing an assay medium, the second compartment being adapted to maintain the assay medium separate from the biological indicator during the sterilization process, and the second compartment being adapted to permit the assay medium to flow into contact with the biological indicator after the biological indicator has been exposed to the sterilant, the biological indicator and the assay medium forming a dielectric between the electrical conductors. In an embodiment, the capacitance device is connected to a sensing apparatus for ascertaining the effectiveness of the sterilization process. The sensing apparatus may comprise a control unit, an indicator, and a sensor. In an embodiment, the capacitance device is connected to a capacitance bridge. The capacitance bridge may have an accuracy level of about 1 µF or less. In an embodiment, the capacitance of the dielectric is in the range from about 0.1 nF to about 20 mF, or about 1 to about 5000 nF. In an embodiment, the test microorganisms comprise bacteria. In an embodiment, the test microorganisms comprise spores. In an embodiment, the test microorganisms comprise bacterial spores. In an embodiment, the test microorganisms comprise spores on a carrier. The test microorganism population on the carrier may be in the range from about 500,000 to about 4,000,000 colony forming units. In an embodiment, the carrier comprises paper, plastic, glass, ceramics, metal foil, one or both conductors of the capacitor, or a combination of two or more thereof. In an embodiment, each electrical conductor has a length in the range from about 1 to about 5 cm, and a width in the range from about 0.5 to about 3 cm. In an embodiment, the separation between the electrical conductors is in the range from about 0.5 to about 5 mm.

This invention relates to a process for analyzing a biological indicator, comprising: placing the biological indicator and an assay medium in a capacitor, the biological indicator comprising test microorganisms, the capacitor comprising two electrical conductors, the biological indicator and the assay medium being placed between the two conductors and forming a dielectric for the capacitor; applying an electrical signal to the conductors; measuring the capacitance of the capacitor; and determining from the capacitance of the capacitor whether any of the test microorganisms are alive. In an embodiment, the capacitor is connected to a capacitance bridge. The capacitance bridge may have an accuracy level of about 1 µF or less. In an embodiment, the capacitance of the dielectric is in the range from about 0.1 nF to about 20 mF, or about 1 to about 5,000 nF. In an embodiment, the test microorganisms comprise bacteria. In an embodiment, the test microorganisms comprise spores. In an embodiment, the test microorganisms comprise bacterial spores. In an embodiment, the test microorganisms are on a carrier, the test microorganism population on the carrier being in the range from about 500,000 to about 4,000,000 colony forming units. In an embodiment, the test microorganisms comprise spores and the spores are on a carrier. The spore population on the carrier may be in the range from about 500,000 to about 4,000,000 spores. In an embodiment, the test microorganisms are on a carrier, the carrier comprising paper, plastic, glass, ceramics, metal foil, one or both conductors of the capacitor, or a combination of two or more thereof. In an embodiment, each electrical conductor has a length in the range from about 1 to about 5 cm, and a width in the range from about 0.5 to about 3 cm. In an embodiment, the separation between the electrical conductors provided by the gap is in the range from about 0.5 to about 5 mm. In an embodiment, all of the test microorganisms are dead. In an embodiment, some of the test microorganisms are alive, the number of live test microorganisms being in the range from 1 to about 4,000,000, or from 1 to about 2,000,000, or from 1 to about 1,000,000, or from 1 to about 100,000, or from 1 to about 50,000, or from 1 to about 10,000 colony forming units.

This invention relates to a process for determining the efficacy of a sterilization process, comprising: exposing an article to be sterilized and a biological indicator to a sterilant, the biological indicator comprising test microorganisms; placing the biological indicator and an assay medium in a capacitor, the capacitor comprising two electrical conductors, the biological indicator and the assay medium being positioned between the two electrical conductors and comprising a dielectric for the capacitor; applying an electrical signal to the conductors; measuring the capacitance of the capacitor; and determining from the capacitance of the capacitor whether any of the test microorganisms are alive. In an embodiment, the sterilant comprises vaporous hydrogen peroxide, steam, ethylene oxide, peracetic acid, ozone, ultraviolet light, radiation, or a combination of two or more thereof. In an embodiment, the capacitor is connected to a capacitance bridge. The capacitance bridge may have an accuracy level of about 1 µF or less. In an embodiment, the capacitance of the dielectric is in the range from about 0.1 nF to about 20 mF, or about 1 to about 5000 nF. In an embodiment, the test microorganisms comprise bacteria. In an embodiment, the test microorganisms comprise spores. In an embodiment, the test microorganisms comprise bacterial spores. In an embodiment, the test microorganisms are on a carrier. The test microorganism population on the carrier may be in the range from about 500,000 to about 4,000,000 colony forming units. In an embodiment, the carrier comprises paper, plastic, glass, ceramics, metal foil, one or both conductors of the capacitor, or a combination of two or more thereof. In an embodiment, each electrical conductor has a length in the range from about 1 to about 5 cm, and a width in the range from about 0.5 to about 3 cm. In an embodiment, the separation between the electrical conductors is in the range from about 0.5 to about 5 mm. In an embodiment, all of the test microorganisms are dead. In an embodiment, some of the test microorganisms are alive, the number of live test microorganisms being in the range from 1 to about 4,000,000, or 1 to about 2,000,000, or 1 to about 1,000,000, or 1 to about 100,000, or from 1 to about 50,000, or from 1 to about 10,000 colony forming units.

This invention relates to a process for determining the efficacy of a sterilization process, comprising: (a) exposing an article to be sterilized and a biological indicator to a sterilant, the biological indicator comprising test microorganisms and being positioned in a capacitor, the capacitor comprising two electrical conductors, the biological indicator being positioned between the two electrical conductors and comprising a dielectric for the capacitor; (b) positioning an assay medium between the electrical conductors in contact with the biological indicator to form a dielectric for the capacitor; (c) applying an electrical signal to the conductors; (d) measuring the capacitance of the capacitor; and (e) determining from the capacitance of the capacitor whether any of the test microorganisms are alive. In an embodiment, the sterilant comprises vaporous hydrogen peroxide, steam, ethylene oxide, peracetic acid, ozone, ultraviolet light, radiation, or a combination of two or more thereof. In an embodiment, the capacitor is connected to a capacitance bridge. The capacitance bridge may have an accuracy level of about 1 µF or less. In an embodiment, the capacitance of the dielectric is in the range from about 0.1 nF to about 20 mF, or about 1 to about 5000 nF. In an embodiment, the test microorganisms comprise bacteria. In an embodiment, the test microorganisms comprise spores. In an embodiment, the test microorganisms comprise spores and the spores comprise bacterial spores. In an embodiment, the test microorganisms are on a carrier. The test microorganism population on the carrier may be in the range from about 500,000 to about 4,000,000 colony forming units. In an embodiment, the carrier comprises paper, plastic, glass, ceramics, metal foil, one or both conductors of the capacitor, or a combination of two or more thereof. In an embodiment, each electrical conductor has a length in the range from about 1 to about 5 cm, and a width in the range from about 0.5 to about 3 cm. In an embodiment, the separation between the electrical conductors is in the range from about 0.5 to about 5 mm. In an embodiment, all of the test microorganisms are dead. In an embodiment, some of the test microorganisms are alive, the number of live test microorganisms being in the range from 1 to about 4,000,000, or 1 to about 2,000,000, or 1 to about 1,000,000, or 1 to about 100,000, or from 1 to about 50,000, or from 1 to about 10,000 colony forming units. In an embodiment, during step (a) the article to be sterilized and the biological indicator are positioned in an enclosure while being exposed to the sterilant, and during steps (b), (c), (d) and (e) the biological indicator is positioned within the enclosure. In an embodiment, during step (a) the article to be sterilized and the biological indicator are positioned in an enclosure while being exposed to the sterilant, and during steps (b), (c), (d) and (e) the biological indicator is removed from the enclosure.

This invention relates to a process for counting test microorganisms on a treated biological indicator using a capacitance test system comprising a capacitor and a capacitance bridge, the process comprising: (a) calibrating the capacitance test system to establish (1) an all dead capacitance control value using an all dead control biological indicator containing test microorganisms where all of the test microorganisms are dead, and (2) an all live capacitance control value using a live control biological indicator containing test microorganisms where all of the test microorganisms are alive, the all dead control biological indicator and the all live control biological indicator being the same except for the presence of dead or live test microorganisms, the all dead and all live control biological indicators having the same estimated number of test microorganisms; (b) determining the difference between the all live capacitance control value and the all dead capacitance control value to obtain a net capacitance control value; (c) dividing the net capacitance control value by the estimated number of test microorganisms on the all live control biological indicator to obtain a capacitance value for each test microorganism; (d) determining the capacitance value for a treated biological indicator; (e) determining the difference between the capacitance value for the treated biological indicator in (d) and the all dead capacitance control value in (a) to obtain a net capacitance treated value; and (f) dividing the net capacitance treated value in (e) by the capacitance value for each test microorganism in (c) to obtain the number of live test microorganisms on the treated biological indicator. This invention relates to a process for counting spores on a treated biological indicator using a capacitance test system comprising a capacitor and a capacitance bridge, the process comprising: (a) calibrating the capacitance test system to establish (1) an all dead capacitance control value using an all dead control biological indicator containing spores where all of the spores are dead, and (2) an all live capacitance control value using a live control biological indicator containing spores where all of the spores are alive, the all dead control biological indicator and the all live control biological indicator being the same except for the presence of dead and live spores, the all dead and all live control biological indicators having the same estimated number of spores; (b) determining the difference between the all live capacitance control value and the all dead capacitance control value to obtain a net capacitance control value; (c) dividing the net capacitance control value by the estimated number of spores on the all live control biological indicator to obtain a capacitance value for each spore; (d) determining the capacitance value for a treated biological indicator; (e) determining the difference between the capacitance value for the treated biological indicator in (d) and the all dead capacitance control value in (a) to obtain a net capacitance treated value; and (f) dividing the net capacitance treated value in (e) by the capacitance value for each spore in (c) to obtain the number of live spores on the treated biological indicator. In an embodiment, the all dead capacitance control value is higher than the all live capacitance control value. In an embodiment, the all dead capacitance control value is lower than the all live capacitance control value. In an embodiment, the capacitance bridge has an accuracy level of about 1 µF or less. In an embodiment, the capacitor comprises a dielectric, the capacitance of the dielectric being in the range from about 0.1 nF to about 20 mF, or about 1 to about 5,000 nF. In an embodiment, the spores on the all dead control biological indicator, the all live control biological indicator, and the treated biological indicator comprise bacterial spores. In an embodiment, the spores on the all dead control biological indicator, the all live control biological indicator, and the treated biological indicator comprise spores of the *Bacillus* or Clostridia genera. In an embodiment, the spores on the all dead control biological indicator, the all live control biological indicator, and the treated biological indicator comprise spores of *Geobacillus stearothermophilus, Bacillus atrophaeus, Bacillus sphaericus, Bacillus anthracis, Bacillus pumilus, Bacillus coagulans, Clostridium sporogenes, Clostridium difficile, Clostridium botulinum, Bacillus subtilis globigii, Bacillus cereus, Bacillus circulans*, or a mixture of two or more thereof. In an embodiment, the spores on the all dead control biological indicator, the all live control biological indicator, and the treated biological indicator comprise *Geobacillus stearothermophilus* spores, *Bacillus atrophaeus* spores, or a combination thereof. In an embodiment, the all dead control biological indicator, the all live control biological indicator, and the treated biological indicator comprise spores on a carrier, the spore population on the carrier for each biological indicator being in the range from about 500,000 to about 4,000,000 spores. In an embodiment, the capacitor comprises two electrical conductors, and the all dead control biological indicator, the all live control biological indicator and the treated biological indicator comprise spores on a carrier, the carrier for each biological indicator comprising paper or plastic, glass, ceramics, metal foil, one or both conductors of the capacitor, or a combination of two or more thereof. In an embodiment, the all dead control biological indicator, the all live control biological indicator and the treated biological indicator comprise spores on a carrier, the carrier for each biological indicator having a length in the range from about 1 to about 5 cm, a width in the range from about 0.1 to about 1 cm, and a thickness in the range from about 0.5 to about 3 mm. In an embodiment, the capacitor comprises electrical conductors, the electrical conductors being made of aluminum, copper, silver, gold, platinum, or a combination of two or more thereof. In an embodiment, the electrical conductors comprise indium tin oxide (ITO) plates where indium tin oxide is deposited on glass plates. In an embodiment, the capacitor comprises two electrical conductors, each electrical conductor having a length in the range from about 1 to about 5 cm, and a width in the range from about 0.5 to about 3 cm. In an embodiment, the capacitor comprises two electrical conductors, the separation between the electrical conductors being in the range from about 0.5 to about 5 mm. In an embodiment, the test microorganisms are spores and all of the spores on the treated biological indicator are dead. In an embodiment, the test microorganisms are spores and some of the spores on the treated biological indicator are alive, the number of live spores being in the range from 1 to about 4,000,000, or 1 to about 2,000,000, or 1 to about 1,000,000, or 1 to about 100,000, or from 1 to about 50,000, or from 1 to about 10,000.

In an embodiment, the all dead capacitance control value is in the range from about 0.1 nF to about 20 mF. In an embodiment, the all live capacitance control value is in the range from about 0.1 nF to about 20 mF. In an embodiment, the capacitance value for each test microorganism or spore is in the range up to about 10 pF. In an embodiment, live test microorganisms or spores are detected within a period of time of up to about 2000 seconds. In an embodiment, it is determined that all test microorganisms or spores are dead within a period of time of up to about 2000 seconds.

This invention relates to a method for determining the efficacy of a sterilization process, said method comprising: placing spores within a region containing at least one item to be sterilized; exposing the at least one item and the spores to a sterilant; after exposure to the sterilant, placing the spores in an assay medium located between a pair of electrical conductors, wherein the spores and assay medium serve as a dielectric of a capacitor; measuring the capacitance of the capacitor; and determining whether the measured capacitance falls within a first range of capacitance values indicative of the presence of live spores or falls within a second range of capacitance values indicative of the presence of dead spores, wherein the first range of capacitance values does not overlap with the second range of capacitance values. In an embodiment, the spores are *Geobacillus stearothermophilus* spores, *Bacillus atrophaeus* spores, or a combination thereof. In an embodiment, the assay medium comprises glycerol. In an embodiment, the assay medium comprises about 20% by volume glycerol in water. In an embodiment, the biological indicator is an instant read biological indicator. In an embodiment, the capacitor is a parallel plate capacitor. In an embodiment, the sterilant is steam.

This invention relates to a biological indicator comprising: a capacitive sensor including a capacitor having a pair of electrical conductors and a dielectric comprised of an assay medium and a plurality of spores that have been exposed to a sterilant; and a control unit having a memory pre-stored with data associated with a first range of capacitance values indicative of the presence of live spores and data associated with a second range of capacitance values indicative of the presence of dead spores, wherein the first range of capacitance values does not overlap with the second range of capacitance values. In an embodiment, the spores are *Geobacillus stearothermophilus* spores, *Bacillus atrophaeus* spores, or a combination thereof. In an embodiment, the assay medium comprises glycerol. In an embodiment, the assay medium comprises about 20% by volume glycerol in water. In an embodiment, the biological indicator is an instant read biological indicator. In an embodiment, the capacitor is a parallel plate capacitor. In an embodiment, the sterilant is steam.

This invention relates to a system for determining the efficacy of a sterilization process, comprising: a plurality of spores that have been exposed to a sterilant; an assay medium; a capacitive sensor including a capacitor having a pair of electrical conductors and a dielectric comprised of the assay medium and the plurality of spores; and a control unit having a memory pre-stored with data associated with a first range of capacitance values indicative of the presence of live spores and data associated with a second range of capacitance values indicative of the presence of dead spores, wherein the first range of capacitance values does not overlap with the second range of capacitance values. In an embodiment, the spores are *Geobacillus stearothermophilus* spores, *Bacillus atrophaeus* spores, or a combination thereof. In an embodiment, the assay medium comprises glycerol. In an embodiment, the assay medium comprises about 20% by volume glycerol in water. In an embodiment, the biological indicator is an instant read biological indicator. In an embodiment, the capacitor is a parallel plate capacitor. In an embodiment, the sterilant is steam.

This invention relates to a process for counting microorganisms on a carrier using a capacitance test system comprising a capacitor and a capacitance bridge, the process comprising: (a) establishing a capacitance value for the carrier; (b) establishing a capacitance value for the carrier with a control deposit on the carrier of a known quantity of microorganisms; (c) determining the difference between the capacitance value in (b) and the capacitance value in (a) to obtain a net capacitance value for the known quantity of microorganisms in (b); (d) dividing the net capacitance value for the known quantity of microorganisms in (c) by the known quantity of microorganisms in (b) to obtain a capacitance value for each microorganism; (e) determining a capacitance value for the carrier with a test deposit of microorganisms on the carrier; (f) determining the difference between the capacitance value for the carrier with the test deposit of microorganisms in (e) and the capacitance value for the carrier in (a) to obtain a net capacitance test value; and (g) dividing the net capacitance test value in (f) by the capacitance value for each microorganism in (d) to obtain the number of microorganisms in the test deposit of microorganisms in (e). Those skilled in the art will recognize that the carrier referred to in steps (a), (b) and (e) may not be the exact same carrier for each step, but each will at least be identical or comparable samples of the same carrier. In an embodiment, the known quantity of microorganisms in (b) is in the range from about 500,000 to about 4,000,000 colony forming units. In an embodiment, the number of microorganisms in the test deposit of microorganisms in (g) is in the range from 1 to about 4,000,000 colony forming units. In an embodiment, the capacitance value for the carrier with the control deposit of the known quantity of microorganisms in (b) is in the range from about 0.1 nF to about 20 mF. In an embodiment, the capacitance value for each microorganism in (d) is up to about 10 pF, or in the range from about 0.05 to about 2 pF.

This invention relates to a process for counting spores on a carrier using a capacitance test system comprising a capacitor and a capacitance bridge, the process comprising: (a) establishing a capacitance value for the carrier; (b) establishing a capacitance value for the carrier with a control deposit on the carrier of a known quantity of spores; (c) determining the difference between the capacitance value in (b) and the capacitance value in (a) to obtain a net capacitance value for the known quantity of spores in (b); (d) dividing the net capacitance value for the known quantity of spores in (c) by the known quantity of spores in (b) to obtain a capacitance value for each spore; (e) determining a capacitance value for the carrier with a test deposit of spores on the carrier; (f) determining the difference between the capacitance value for the carrier with the test deposit of spores in (e) and the capacitance value for the carrier in (a) to obtain a net capacitance test value; and (g) dividing the net capacitance test value in (f) by the capacitance value for each spore in (d) to obtain the number of spores in the test deposit of spores in (e). Those skilled in the art will recognize that the carrier referred to in steps (a), (b) and (e) may not be the exact same carrier for each step, but each will at least be identical or comparable samples of the same carrier. In an embodiment, the capacitance bridge has an accuracy level of about 1 µF or less. In an embodiment, the capacitor comprises a dielectric, the capacitance of the dielectric being in the range from about 0.1 nF to about 20 mF. In an embodiment, the spores comprise bacterial spores. In an embodiment, the spores comprise spores of the *Bacillus* or Clostridia genera. In an embodiment, the spores comprise spores of *Geobacillus stearothermophilus, Bacillus atrophaeus, Bacillus sphaericus, Bacillus anthracis, Bacillus pumilus, Bacillus coagulans, Clostridium sporogenes, Clostridium difficile, Clostridium botulinum, Bacillus subtilis* globigii, *Bacillus cereus, Bacillus circulans*, or a mixture of two or more thereof. In an embodiment, the spores comprise *Geobacillus stearothermophilus* spores, *Bacillus atrophaeus* spores, or a mixture thereof. In an embodiment, the known quantity of spores in (b) is in the range from about 500,000 to about 4,000,000 spores. In an embodiment, the carrier comprises paper, plastic, glass, ceramics, metal foil, one or both conductors of the capacitor, or a combination of two or more thereof. In an embodiment, the carrier has a length in the range from about 1 to about 5 cm, a width in the range from about 0.1 to about 1 cm, and a thickness in the range from about 0.5 to about 3 mm. In an embodiment, the capacitor comprises electrical conductors, the electrical conductors comprise aluminum, copper, silver, gold, platinum, or a combination of two or more thereof. In an embodiment, the capacitor comprises electrical conductors, the electrical conductors comprising indium tin oxide on glass. In an embodiment, the capacitor comprises two electrical conductors, each electrical conductor having a length in the range from about 1 to about 5 cm, and a width in the range from about 0.5 to about 3 cm. In an embodiment, the capacitor comprises two electrical conductors, the separation between the electrical conductors being in the range from about 0.5 to about 5 mm. In an embodiment, the number of spores in the test deposit of spores is in the range from 1 to about 4,000,000. In an embodiment, the capacitance value for the carrier is in the range from about 0.1 nF to about 20 mF. In an embodiment, the capacitance value for the carrier with the control deposit of the known quantity of spores in (b) is in the range from about 0.1 nF to about 20 mF. In an embodiment, the capacitance value for each spore is in the range up to about 10 pF, or from about 0.05 to about 2 pF.

With this invention, it is possible to determine whether live test microorganisms (e.g., spores) are present on a biological indicator that has been subjected to a sterilization, and if so, how many. The determination of whether live test microorganisms or spores are present can be determined instantaneously, or within a period of time of up to about 2000 seconds, or up to about 1500 seconds, or up to about 1000 seconds, or up to about 500 seconds, or up to about 200 seconds, or up to about 100 seconds, or up to about 50 seconds, or up to about 30 seconds, or in the range from about 5 to about 2000 seconds, or from about 10 to about 1800 seconds, or from about 20 to about 1500 seconds, or from about 30 to about 1200 seconds, or from about 50 to about 1000 seconds, or from about 60 to about 800 seconds.

This invention relates to a process for counting microorganisms in a liquid using a capacitance test system comprising a capacitor and a capacitance bridge, the process comprising: (a) establishing a capacitance value for the liquid; (b) establishing a capacitance value for the liquid in (a) with a control sample of a known quantity of microorganisms in the liquid; (c) determining the difference between the capacitance value in (b) and the capacitance value in (a) to obtain a net capacitance value for the known quantity of microorganisms in (b); (d) dividing the net capacitance value for the known quantity of microorganisms in (c) by the known quantity of microorganisms in (b) to obtain a capacitance value for each microorganism; (e) determining a capacitance value for the liquid in (a) with a test sample of microorganisms in the liquid; (f) determining the difference between the capacitance value for the liquid with the test sample of microorganisms in (e) and the capacitance value for the liquid in (a) to obtain a net capacitance test value; and (g) dividing the net capacitance test value in (f) by the capacitance value for each microorganism in (d) to obtain the number of microorganisms in the test sample of microorganisms in (e). In an embodiment, the capacitor comprises two electrical conductors and during step (e) the test sample of microorganism is positioned between the conductors and forms a dielectric for the capacitor. In an embodiment, the capacitor comprises two electrical conductors and during step (e) the test sample of microorganism flows between the conductors and forms a dielectric for the capacitor. In an embodiment, the concentration of microorganisms in the test sample of microorganism in the liquid in (e) is determined by dividing the number of microorganisms in the test sample of microorganisms in (e) by the volume of the liquid in (e). In an embodiment, the known quantity of microorganisms in (b) is in the range from about 500,000 to about 4,000,000 colony forming units. In an embodiment, the number of microorganisms in the test sample of microorganisms in (g) is in the range from 1 to about 4,000,000 colony forming units. In an embodiment, the capacitance value for the liquid with the control sample of the known quantity of microorganisms in (b) is in the range from about 0.1 nF to about 20 mF. In an embodiment, the capacitance value for each microorganism in (d) is in the range up to about 10 pF. In an embodiment, the capacitance bridge has an accuracy level of about 1 µF or less. In an embodiment, the microorganisms comprise bacteria, archaea, protozoa, fungi, algae, virus, hetminths, or a combination of two or more thereof. In an embodiment, the microorganisms comprise bacteria. In an embodiment, the microorganisms comprise bacterial spores. In an embodiment, the spores comprise spores of the *Bacillus* or Clostridia genera. In an embodiment, the spores comprise spores of *Geobacillus stearothermophilus, Bacillus atrophaeus, Bacillus sphaericus, Bacillus anthracis, Bacillus pumilus, Bacillus coagulans, Clostridium sporogenes, Clostridium difficile, Clostridium botulinum, Bacillus subtilis* globigii, *Bacillus cereus, Bacillus circulans*, or a mixture of two or more thereof. In an embodiment, the spores comprise *Geobacillus stearothermophilus* spores, *Bacillus atrophaeus* spores, or a mixture thereof. In an embodiment, the microorganisms comprise yeast or *lactobacillus* microorganisms. In an embodiment, the capacitor comprises electrical conductors, the electrical conductors comprise aluminum, copper, silver, gold, platinum, or a combination of two or more thereof. In an embodiment, the capacitor comprises electrical conductors, the electrical conductors comprising indium tin oxide on glass. In an embodiment, the capacitor comprises two electrical conductors, each electrical conductor having a length in the range from about 1 to about 5 cm, and a width in the range from about 0.5 to about 3 cm. In an embodiment, the capacitor comprises two electrical conductors, the separation between the electrical conductors being in the range from about 0.5 to about 5 mm.

BRIEF DESCRIPTION OF THE DRAWINGS

In the annexed drawings, like parts and features have like designations.

DETAILED DESCRIPTION

Figure 1:
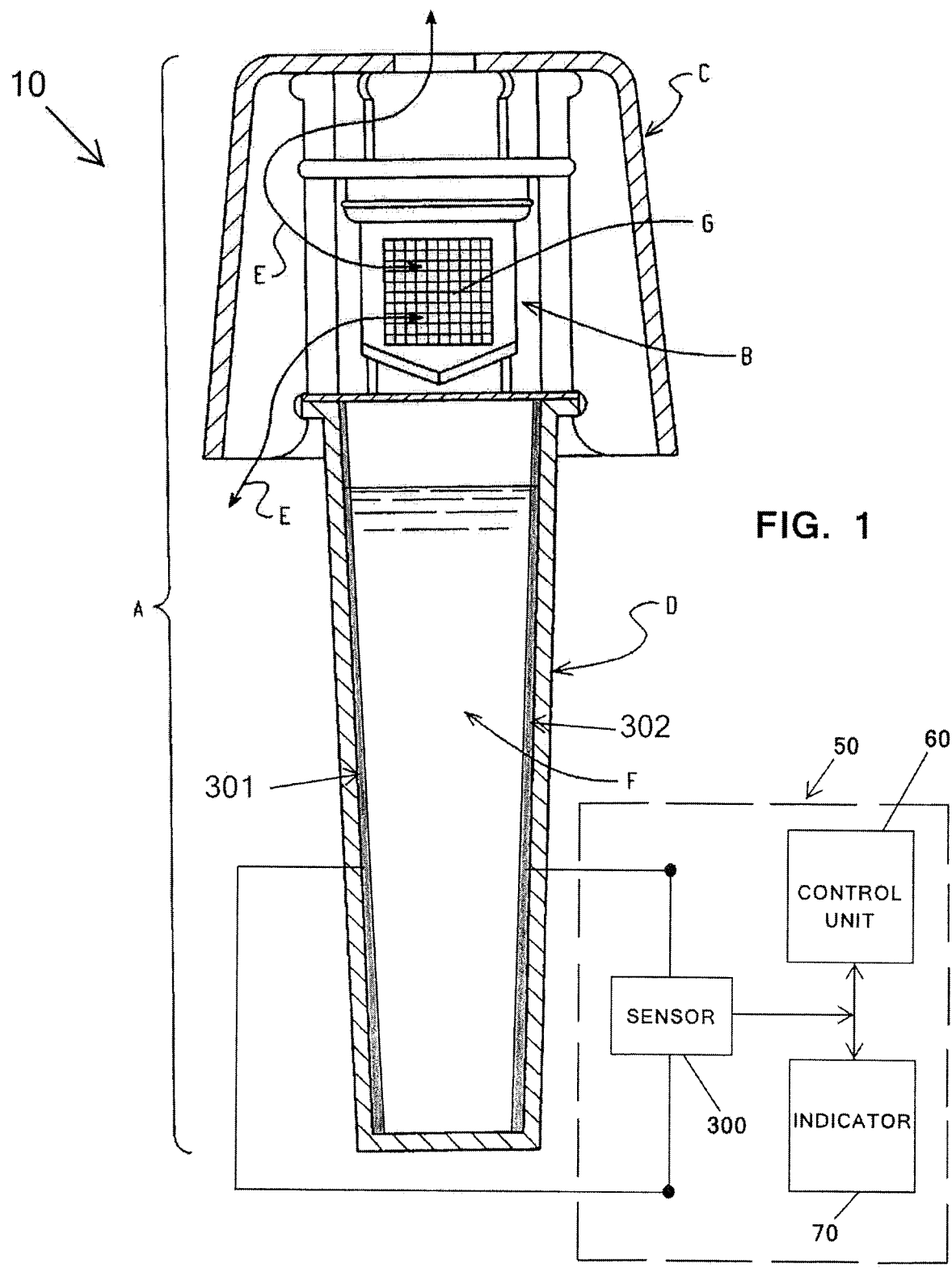
FIG. 1 is a sectional view taken from the side of a capacitor configured with a sensing apparatus according to an embodiment of the present invention.

All ranges and ratio limits disclosed in the specification and claims may be combined in any manner. It is to be understood that unless specifically stated otherwise, references to "a," "an," and/or "the" may include one or more than one, and that reference to an item in the singular may also include the item in the plural.

The phrase "and/or" should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The word "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," may refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

The phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The transitional words or phrases, such as "comprising," "including," "carrying," "having," "containing," "involving," "holding," and the like, are to be understood to be open-ended, i.e., to mean including but not limited to.

The term "capacitor" refers to a two-terminal electrical component used to store electrical energy temporarily. The capacitor provided by the present invention comprises two electrical conductors separated by a dielectric.

The term "dielectric" refers to an electrical insulator that can be polarized by an applied electrical field. When a dielectric is placed on an electrical field, electric charges do not flow through the material as they do a conductor, but only slightly shift from their average equilibrium positions causing dielectric polarization. The dielectric may comprise microorganisms. The dielectric may comprise microorganisms in combination with an assay fluid. The dielectric may comprise test microorganisms. The dielectric may comprise bacteria. The dielectric may comprise spores. The dielectric may comprise a biological indicator. The dielectric may comprise a biological indicator in combination with an assay medium.

The term "microorganism" refers to a microscopic living organism. The microorganisms may be unicellular, multicellular, or in the form of cell clusters. The microorganisms may comprise bacteria, archaea, protozoa, fungi, algae, viruses, multicellular animal parasites (helminths), or a combination of two or more thereof. The microorganisms may comprise spores. The microorganisms may comprise bacterial spores. The microorganisms may comprise spores of the *Bacillus* or Clostridia genera. The microorganisms may comprise spores of *Geobacillus stearothermophilus, Bacillus atrophaeus, Bacillus sphaericus, Bacillus anthracis, Bacillus pumilus, Bacillus coagulans, Clostridium sporogenes, Clostridium difficile, Clostridium botulinum, Bacillus subtilis* globigii, *Bacillus cereus, Bacillus circulans*, or a mixture of two or more thereof. The microorganisms may comprise *Geobacillus stearothermophilus* spores, *Bacillus atrophaeus* spores, or a mixture thereof. The microorganisms may comprise yeast or *lactobacillus* microorganisms. In an embodiment, the term "microorganism" does not include red or white blood cells (e.g., bovine blood).

The term "bacteria" refers to a domain of prokaryotic microorganisms. The bacteria may be unicellular microorganisms. The cells may be described as prokaryotic because they lack a nucleus. The bacteria cells may have one of four major shapes: *bacillus* (rod shaped), coccus (spherical shape), spirilla (spiral shape), or *vibrio* (curved shape). The bacteria may have a peptidoglycan wall. The bacteria may divide by bacteria fission. The bacteria may possess flagella for motility. The bacteria may be classified as either Gram-positive or Gram-negative when using Gram staining. The bacteria may be divided based on their response to gaseous oxygen into the following groups: aerobic (living in the presence of oxygen), anaerobic (living without oxygen), and facultative anaerobic (can live in both environments). The bacteria may be classified as heterotrophs or autotrophs. Autotrophs make their own food by using the energy of sunlight or chemical reactions, in which case they are called chemoautotrophs. Heterotrophs obtain their energy by consuming other organisms. The bacteria that use decaying life forms as a source of energy may be called saprophytes.

The term "spore" refers to a unit of asexual reproduction that may be adapted for dispersal and survival for extended periods of time under unfavorable conditions. Spores are highly resistant, dormant cell types. Endospores (or simply spores) form within the vegetative mother cell in response to adverse changes in the environment, most commonly nutrient depletion. The mother cell undergoes an asymmetrical cell division, where it replicates its genetic material, which is then surrounded by multiple concentric and spore specific layers. The mother cell then disintegrates, releasing the mature dormant spore which requires neither nutrients, water nor air for survival and is protected against a variety of trauma, including extremes of temperature, radiation, and chemical assault.

The term "bacterial spore" refers to a spore produced by bacteria.

The term "test microorganism" refers to a microorganism that may be used to test the efficacy of a sterilization process. The test microorganism may be more resistant to a sterilization process than the organisms intended for destruction during the sterilization process. In theory, if the test microorganisms were to die during a sterilization process, then all organisms intended for destruction during the sterilization process that are less resistant to the sterilization than the test microorganisms would also die. The test microorganisms may comprise bacteria. The test microorganisms may comprise spores. The test microorganisms may comprise bacterial spores. The test microorganisms may comprise spores of the *Bacillus* or Clostridia genera. The test microorganisms may comprise spores of *Geobacillus stearothermophilus, Bacillus atrophaeus, Bacillus sphaericus, Bacillus anthracis, Bacillus pumilus, Bacillus coagulans, Clostridium sporogenes, Clostridium difficile, Clostridium botulinum, Bacillus subtilis globigii, Bacillus cereus, Bacillus circulans*, or a mixture of two or more thereof. The test microorganisms may comprise *Geobacillus stearothermophilus* spores, *Bacillus atrophaeus* spores, or a mixture thereof.

The term "biological indicator" refers to an article or a material that can be used to determine the efficacy of a sterilization process. The biological indicator may comprise test microorganisms (e.g., bacteria, spores or bacterial spores). The biological indicator may comprise test microorganisms on a carrier. The biological indicator may comprise bacteria, the bacteria may be present within a defined space or deposited on a carrier. The biological indicator may comprise spores (e.g., bacterial spores), the spores may be present within a defined space or on a carrier. The biological indicator may comprise a spore strip.

The term "carrier" refers to a support onto which microorganisms may be deposited.

The term "killing" microorganisms or spores refers to rendering microorganisms or spores incapable of reproduction, metabolism and/or growth. The term "dead" microorganisms or spores refers to microorganisms or spores which have been rendered incapable of reproduction, metabolism and/or growth. The microorganisms or spores used with a biological indicator may be selected from those that would be more resistant to a sterilization process for which they are intended to monitor than the organisms to be killed by the sterilization process. The killing of the microorganisms or spores of the biological indicator during a sterilization process is indicative of a successful sterilization process.

The term "live" microorganisms or spores refers to microorganisms or spores that are capable of reproduction, metabolism and/or growth.

The term "Farad" (F) refers to a unit of electrical capacitance. Electrical capacitance is a measure of the ability of a body to store an electrical charge. One Farad is the capacitance across which, when charged with one coulomb, there is a potential difference of one volt. For many applications, the Farad is an impractically large unit of capacitance. As such, for many electrical and electronics applications, the following prefixes are used: 1 mF (milli Farad)=$10^{-3}$ Farad; 1 µF (micro Farad)=$10^{-6}$ Farad; 1 nF (nano Farad)=$10^{-9}$ Farad; 1 pF (pico Farad)=$10^{-12}$ Farad; 1 fF (femto Farad) =$10^{-15}$ Farad; and 1 aF (atto Farad)=$10^{-18}$ Farad.

The term "log reduction" is a mathematical term to show the number of live microorganisms or spores killed by contacting the microorganisms or spores with a sterilant during a sterilization process. A "4 log reduction" means that the number of live microorganisms or spores at the end of the sterilization process is reduced by 10,000-fold. A "5 log reduction" means that the number of live microorganisms or spores is reduced by 100,000-fold. A "6 log reduction" means that the number of live microorganisms or spores is reduced by 1,000,000-fold. Thus, for example, if a carrier has 1,000,000 live microorganisms or spores on it, a 6-log reduction would reduce the number of live microorganisms or spores to 1.

The term "sterilization" may be used to refer to a process wherein there is a total absence of living test microorganisms remaining after the sterilization process has been completed. However, processes that are less rigorous than sterilization processes including, for example, disinfection, sanitization, decontamination, cleaning processes, and the like, may be of value and are taken into account with this invention. Unless otherwise indicated, the term "sterilization" is used herein to refer to sterilization processes as well as less rigorous processes such as disinfection, sanitation, decontamination, cleaning, and the like.

The term "sterilant" refers to any medium or energy that can be used to sterilize a substrate (e.g., a medical device, the interior of a room, etc.). The sterilant may comprise a liquid or a gas. The sterilant may comprise vaporous hydrogen peroxide, steam, ethylene oxide, peracetic acid, ozone, or a combination of two or more thereof. The sterilant may comprise ultraviolet light or radiation. The radiation may comprise x-ray radiation, gamma radiation, or electron beam radiation.

The sterilization process provided for herein may employ any sterilant. The sterilization process may be conducted for an effective period of time to achieve at least a 4 log reduction, or at least a 5 log reduction, or at least a 6 log reduction in the number of test microorganisms capable of reproduction, metabolism and/or growth. When at least a 6 log reduction is achieved, the process may be referred to as a sterilization process. When a 4 log reduction or a 5 log reduction is achieved, the process may be considered to be less rigorous than a sterilization process, but nevertheless useful for various disinfection, sanitization, decontamination and/or cleaning applications.

The biological indicator may comprise test microorganisms (e.g., spores) deposited on a carrier. The test microorganism population for the biological indicator may be in the range from about 500,000 to about 4,000,000 colony forming units (cfu), or from about 500,000 to about 2,500,000 cfu, or from about 500,000 to about 1,500,000 cfu, or from about 750,000 to about 1,200,000 cfu, or about $10^6$ cfu. If the test microorganisms are spores, the spore population for the biological indicator may be in the range from about 500,000 to about 4,000,000 spores, or from about 500,000 to about 2,500,000 spores, or from about 500,000 to about 1,500,000 spores, or from about 750,000 to about 1,200,000 spores. The spore population may be about $10^6$ spores. The biological indicator may be referred to as a spore test strip.

The spores may comprise bacterial spores. These may include spores of the *Bacillus* or Clostridia genera. The spores may be spores of *Geobacillus stearothermophilus, Bacillus atrophaeus, Bacillus sphaericus, Bacillus anthracis, Bacillus pumilus, Bacillus coagulans, Clostridium sporogenes, Clostridium difficile, Clostridium botulinum, Bacillus subtilis globigii, Bacillus cereus, Bacillus circulans*, or a combination of two or more thereof. The spores may comprise spores of *Geobacillus stearothermophilus, Bacillus atrophaeus*, or a combination thereof.

The carrier may comprise a strip, sheet or film of any material that does not dissolve or deteriorate during the sterilization processes. The carrier may comprise a paper strip, e.g., a cellulose strip, or a plastic sheet or film. The plastic may comprise a polyolefin, polystyrene, polycarbonate, polymethacrylate, polyacrylamide, polyimide, polyester, or a combination of two or more thereof. The carrier may comprise glass, ceramics, metal foil, or a combination of two or more thereof. The carrier may comprise one or both conductors of the capacitor. The carrier may have a length in the range of about 1 to about 5 cm, or about 2 to about 4 cm; a width in the range from about 0.1 to about 1 cm, or about 0.4 to about 0.7 cm; and a thickness in the range from about 0.2 to about 3 mm, or from about 0.5 to about 1.5 mm.

The biological indicator may comprise a spore test strip. These may include *Geobacillus stearothermophilus* test strips for use in monitoring steam sterilizations; *Bacillus atrophaeus* test strips for monitoring ethylene oxide and dry heat sterilizations; *Bacillus pumilus* test strips for irradiation sterilizations; combined species spore test strips, *G. stearothermophilus* and *B. atrophaeus*, for monitoring steam, ethylene oxide and dry heat sterilizations; and the like. These test strips may be characterized by spore populations in the range from about 500,000 to about 4,000,000 spores, or from about 500,000 to about 2,500,000 spores, or from about 500,000 to about 1,500,000 spores, or from about 750,000 to about 1,200,000 spores per test strip, or about $10^6$ spores per test strip.

The biological indicator may comprise a VERIFY® Spore Test Strip for 540® Sterilant Concentrate supplied by STERIS Corporation. This test strip may be used for monitoring liquid chemical sterilizations, e.g., peracetic acid sterilizations. These test strips are characterized by spore populations of at least about $10^5$ *Geobacillus stearothermophilus* spores per test strip.

The capacitor may comprise a passive two-terminal electrical component that has two electrical conductors (plates) separated by a dielectric. The plate area of the capacitor may be in the range from about 0.5 to about 15 $cm^2$, or about 1 to about 10 $cm^2$. The gap between the plates, or the plate separation, may be in the range from about 0.5 to about 5 mm, or from about 1 to about 3 mm. The plates may comprise aluminum, copper, silver, gold, platinum, indium tin oxide deposited on glass, or a combination of two or more thereof. The dielectric may comprise the biological indicator in combination with an assay medium. The biological indicator may comprise a spore test strip.

The assay medium may comprise any fluid (e.g., gas or liquid) that can be combined with the microorganisms, test microorganisms, spores, or biological indicator to form a dielectric for the capacitor. The assay medium may comprise any liquid or gas having a dielectric constant in the range from 1 to about 90, or from about 5 to about 85, or from about 10 to about 80, measured at a temperature in the range from about −10° C. to about 60° C., or about 0° C. to about 50° C., or about 0° C. to about 40° C. The assay medium may comprise air, one or more solvents (e.g., water, dimethyl sulfoxide, deuterium oxide), one or more alcohols or polyols (e.g., methyl alcohol, ethyl alcohol, isopropyl alcohol, butyl alcohol, isoamyl alcohol, hexyl alcohol, octyl alcohol, phenol, biphenyl, benzyl alcohol, creosol, glycol, pentandiol, glycerol), aldehydes (e.g., acetaldehyde, benzaldehyde, butaldehyde, butraldehyde, saliylaldehyde), ketones (e.g., acetone, methylethyl ketone, diethyl ketone, heptone, benzophenone, benzoyl acetone, chloroacetone, cyclohexanone, hexanone), hydrocarbons and halogen substituted hydrocarbons (e.g., chloromethane, bromomethane, benzyl chloride, cyclohexane, cyclohexene, cyclopentane) nitrogenous compounds (e.g., acetonitrile, nitrotoluene, butronitrile, lactonitrile, ammonia, formamide, hydrazine, nitrobenzene, pyridine, proprionitrile, nitrobenzene), anhydrides (e.g., maleic anhydride, butyric anhydride, acetic anhydride), oils (e.g., castor oil), acetates and cyanoacetates (e.g., methylscyanoacetate, methylchloroacetate, ethyl acetoacetate, cyanoethylacetate), thiocyanates (e.g., ethylthiocyanate, amylthiocyanate), hydrocyanic acid, hydrogen peroxide, trifluoroacetic acid, lactic acid, dichloracetic acid, or a mixture of two or more thereof. The assay medium may comprise a glycerol in water solution (e.g., 20% by volume glycerol in water). The assay medium, when combined with the microorganisms or biological indicator may be used in an effective amount to fill the gap between electrical conductors of the capacitor.

In an embodiment, the biological indicator (after it has been exposed to a sterilization process) may be combined with an additional sheet of carrier material (e.g., capacitor paper), two sheets of metal, and an insulating layer, to form a capacitor. The biological indicator may comprise test microorganisms on a carrier, e.g., a spore test strip. The biological indicator may have a thickness of about 0.2 to about 3 mm, or about 0.5 to about 1.5 mm, or about 1 mm. The additional sheet of carrier material may be placed over the biological indicator to cover the test microorganisms. The thickness of the additional sheet of carrier material may be from about 0.0001 to about 0.01 mm, or about 0.001 to about 0.008 mm, or about 0.005 mm. The combined thickness of the biological indicator and the additional sheet of carrier material may be in the range from about 0.21 to about 3.1 mm, or about 0.5 to about 1.5 mm, or about 1 mm. The biological indicator and the additional sheet of carrier material may be square or rectangular in shape with lengths in the range from about 1 to about 5 cm, and widths in the range from about 0.1 to about 1 cm. The biological indicator and additional sheet of carrier material may be placed between the two sheets of metal (e.g., aluminum, copper, gold, silver, platinum, or a combination of two or more thereof) which may be used as electrical conductors. The two sheets of metal may each comprise a metal foil. The two metal sheets may be square or rectangular in shape with lengths of about 1 to about 5 cm, and widths of about 0.5 to about 3 cm. The metal sheets may have thicknesses in the range from about 0.001 to about 0.02 mm, or about 0.003 to about 0.006 mm. The insulating layer may be constructed of paper, a polymer, an elastomer, or a combination of two or more thereof. The insulating layer may have a thickness in the range from about 0.1 to about 5 mm, or about 0.5 to about 1.5 mm. The insulating layer may be square or rectangular in shape with lengths in the range from about 1 to about 5 cm, and widths of about 0.1 to about 1 cm. The biological indicator and the additional sheet of carrier material may be placed between the two sheets of metal, and the resulting construction may then be rolled with the insulating layer positioned between the metal sheets to form a capacitor. The insulating material may be used to avoid shorting. Electrical leads may be placed in contact with the metal sheets.

The capacitor may be connected to a capacitance bridge to detect capacitance levels for the biological indicator. The capacitance bridge may be any capacitance bridge that may detect capacitance levels of about 0.1 nF to about 20 mF, or about 1 to about 5,000 nF, or about 10 to about 2,000 nF, or about 1,500 nF or less. An example of capacitance bridge that may be used is available from Andeen-Hagerling under the trade designation AH2700A. The AH2700A bridge is identified as a 50 Hz-20 kHz capacitance/loss bridge. The AH2700A bridge has the following precision specifications:

| Frequency | Accuracy | Stability | Temperature Coefficient | Resolution | |
|---|---|---|---|---|---|
| kHz | ppm | ppm/year | ppm/° C. | aF | ppm |
| 0.1 | ±9 | ±<1.9 | ±0.07 | 16 | 0.8 |
| 1 | ±5 | ±<1.0 | ±0.035 | 0.8 | 0.16 |
| 10 | ±11 | ±<1.9 | ±0.07 | 2.4 | 0.5 |

The capacitance of the biological indicator can be measured after a sterilization process to determine whether any spores survive the sterilization process and, if so, how many spores survived. The capacitance level readings may be used to determine if all spores are killed, or if 1, 2, 3, etc., spores survived the sterilization process.

For some applications, it may be sufficient to use the capacitor to determine whether all test microorganisms (e.g., spores) of the biological indicator have been killed, or whether any test microorganisms remain alive following a sterilization process. For other applications, it may be of value to count the number of test microorganisms, if any, that survive a sterilization process. With this invention it is possible not to only determine whether or not all test microorganisms of the biological indicator have been killed, but also count the number of test microorganisms that survive a sterilization process and thereby determine what level of sterilization (or disinfection, sanitation, decontamination and/or cleaning) is achieved.

Since results may vary depending on the particular biological indicator and capacitor being used, a "control" can be programmed into the software used in the control unit (discussed below) where the results for the specific biological indicator (e.g., a known commercial spore strip) being used, where all microorganisms are dead, and results for the specific capacitor being used, are stored. By comparing the results for the tested biological indicator and capacitor being used to the control, a capacitance reading can be obtained that can be translated into a reading of the number of live test microorganisms, if any, on the biological indicator being tested.

The number of live test microorganisms, if any, on a treated biological indicator can be determined by the process indicated below. With this process a capacitance test system comprising a capacitor and a capacitance bridge is used. The capacitance test system is initially calibrated using all dead and all live control biological indicators which contain either all dead or all live test microorganisms. The system is then used to evaluate a treated biological indicator which has been subjected to a sterilization. The process involves the following steps: (a) calibrating the capacitance test system to establish (1) an all dead capacitance control value using an all dead control biological indicator containing test organisms or spores where all of the test organisms or spores are dead, and (2) an all live capacitance control value using a live control biological indicator containing test microorganisms or spores where all of the test microorganisms or spores are alive, the all dead control biological indicator and the all live control biological indicator being the same except for the presence of dead or live test microorganisms or spores, the all dead and all live control biological indicators having the same estimated number of test microorganisms or spores; (b) determining the difference between the all live capacitance control value and the all dead capacitance control value to obtain a net capacitance control value; (c) dividing the net capacitance control value by the estimated number of test microorganisms or spores on the all live control biological indicator to obtain a capacitance value for each test microorganism or spore; (d) determining the capacitance value for a treated biological indicator; (e) determining the difference between the capacitance value for the treated biological indicator in (d) and the all dead capacitance control value in (a) to obtain a net capacitance treated value; (f) dividing the net capacitance treated value in (e) by the capacitance value for each test microorganisms or spore in (c) to obtain the number of live test microorganisms or spores on the treated biological indicator.

In performing the above-indicated test procedure, the same biological indicator (e.g., spore strip) type used to calibrate the capacitance test system (i.e., the dead and live control biological indicators) is also used as the treated biological indicator (e.g., treated spore strip), the treated biological indicator having been subjected to a sterilization. Thus, for example, if VERIFY® Spore Test Strip for 540® Sterilant Concentrate supplied by STERIS Corporation are used as the dead and live control biological indicators, then a VERIFY® Spore Test Strip for 540® Sterilant Concentrate supplied by STERIS Corporation will also be used as the treated biological indicator.

The all dead capacitance control value may be from about 0.1 nF to about 20 mF, or from about 1 to about 5,000 nF, or from about 100 to about 2,000 nF, or about 1000 nF. The all live capacitance control value may be from about 0.1 nF to about 20 mF, or about 1 to about 5000 nF, or from about 100 to about 1,000 nf, or about 600 nF. The capacitance value for each test microorganism or spore may be up to about 10 pF, or from about 0.05 pF to about 2 pF, or from about 0.1 to about 1 pF, or about 0.3 pF.

For many sterilizations, the ideal is that no test microorganisms or spores survive the sterilization process. However, if any test microorganisms survive, this process can be used to detect the number that survive. Even if the test microorganisms have not been subjected to a sterilization process, they can nevertheless be counted using the inventive method. This may be applicable to other processes, for example, counting microorganisms in a liquid (e.g., milk, beer, etc.). The number of microorganisms that may be detected and counted may be, for example, from 1 to about 4,000,000 colony forming units (cfu), or from 1 to about 3,000,000 cfu, or from 1 to about 2,000,000 cfu, or from 1 to about 1,000,000 cfu, or from 1 to about 500,000 cfu, or from 1 to about 200,000 cfu, or from 1 to about 100,000 cfu, or from 1 to about 50,000 cfu, or from 1 to about 10000 cfu, or from 1 to about 5000 cfu, or from 1 to about 2000 cfu, or from 1 to about 1000 cfu, or from 1 to about 500 cfu, or from 1 to about 200 cfu, or from 1 to about 100 cfu, or from 1 to about 50 cfu, or from 1 to about 20 cfu, or from 1 to about 10 cfu, or from 1 to about 5 cfu.

The number of spores that may be detected and counted may be, for example, from 1 to about 4,000,000 spores, or from 1 to about 3,000,000 spores, or from 1 to about 2,000,000 spores, or from 1 to about 1,000,000 spores, or from 1 to about 500,000 spores, or from 1 to about 200,000 spores, or from 1 to about 100,000 spores, or from 1 to about 50,000 spores, or from 1 to about 10000 spores, or from 1 to about 5000 spores, or from 1 to about 2000 spores, or from 1 to about 1000 spores, or from 1 to about 500 spores, or from 1 to about 200 spores, or from 1 to about 100 spores, or from 1 to about 50 spores, or from 1 to about 20 spores, or from 1 to about 10 spores, or from 1 to about 5 spores, or from about 5 to about 10000 spores, or from about 5 to about 5000 spores, or from 5 to about 1000 spores, or from 5 to about 500 spores, or from 5 to about 200 spores, or from 5 to about 100 spores, or from 5 to about 50 spores, or from 5 to about 20 spores, or from about 10 to about 10000 spores, or from about 10 to about 5000 spores, or from 10 to about 1000 spores, or from 10 to about 500 spores, or from about 10 to about 200 spores, or from about 10 to about 100 spores, or from about 10 to about 50 spores, or from about 10 to about 30 spores, or from about 15 to about 10000 spores, or from about 15 to about 5000 spores, or from about 15 to about 2000 spores, or from about 15 to about 1000 spores, or from about 15 to about 500 spores, or from about 15 to about 200 spores, or from about 15 to about 100 spores, or from about 15 to about 50 spores, or from about 15 to about 30 spores, or from about 20 to about 10000 spores, or from about 20 to about 5000 spores, or from about 20 to about 1000 spores, or from about 20 to about 500 spores, or from about 20 to about 200 spores, or from about 20 to about 100 spores, or from about 20 to about 50 spores, or from about 20 to about 40 spores, or from about 25 to about 10000 spores, or from about 25 to about 5000 spores, or from about 25 to about 1000 spores, or from about 25 to about 500 spores, or from about 25 to about 200 spores, or from about 25 to about 100 spores, or from about 25 to about 50 spores, or from about 25 to about 40 spores. It is possible with this invention to detect the fact that 1 spore or no spores survive a sterilization process.

The number of test microorganisms, if any, that survive a sterilization process can be determined instantaneously, or within a time period of up to about 2000 seconds, or up to about 1500 seconds, or up to about 1000 seconds, or up to about 500 seconds, or up to about 200 seconds, or up to about 100 seconds, or up to about 50 seconds, or up to about 30 seconds, or from 5 seconds to about 2000 seconds, or from about 10 to about 1800 seconds, or from about 20 to about 1500 seconds, or from about 30 to about 1200 seconds, or from about 50 to about 1000 seconds, or from about 60 to about 800 seconds, or from about 100 to about 600 seconds, or from about 200 to about 600 seconds, or from about 300 to about 600 seconds. This is also applicable to other systems or processes (e.g., liquids such as milk or beer) wherein microorganisms are detected and/or counted.

The biological indicator may be used to release loads or validate sterilization chamber functionality in healthcare settings. In the scientific setting, the biological indicator may be used to validate the functionality of sterilization chambers, release loads of goods, or validate that a process meets required functionality.

The biological indicator may be used by subjecting it to the same sterilant and sterilization conductions as the articles for which sterilization is desired. Following sterilization, the capacitance of the biological indicator may be tested to determine if live test microorganisms or spores survived the sterilization process. If desired, the number of live test microorganisms or spores that survived the sterilization may be determined.

Referring to the drawings, FIG. 1 shows a system 10 comprised of a capacitance device A that includes a biological indicator comprising test microorganisms (e.g., spores) (not shown in FIG. 1), and a sensing apparatus 50 to ascertain the efficacy of a sterilization process. The sensing apparatus 50 may comprise a capacitance bridge. Sensitive capacitance bridges can be inexpensive, making the instant read biological indicator of the present invention a sensitive and inexpensive device.

Capacitance device A includes a biological indicator housing assembly B, a cap C, and an assay medium housing D. A biological indicator comprising test microorganisms (not shown in FIG. 1) is positioned in the housing assembly B. Cap C substantially envelopes the biological indicator housing assembly B. A tortuous path E is defined by the cap C and the housing B between test microorganisms in the biological indicator housing assembly B, and the environment around the capacitance device A. Cap C is movable with respect to assay medium housing D to open and block the tortuous path E. The cap C further provides indirect access for the sterilant to the biological indicator housing B assembly via the tortuous path E. The sterilant may comprise a gaseous sterilant, vaporous sterilant, or a combination thereof. Examples include steam, vaporous hydrogen peroxide, peracetic acid, ozone, ethylene oxide, and the like.

The assay medium housing D defines a holding compartment or reservoir for holding assay medium F. The combination of the biological indicator housing assembly B, the cap C, and the media housing D forms a mechanism that, after a sterilization cycle, is sealed. The test microorganisms are then transferred from the housing assembly B to the assay medium housing D wherein they are immersed into the assay medium F. A pair of electrical conductors (e.g., conducting plates) 301 and 302 are located inside assay medium housing D. The combination of the test microorganisms and the assay medium F forms a dielectric positioned between the conductors 301 and 302.

The tortuous path E discourages external contamination after the internal surfaces and the test microorganisms have been microbially decontaminated. At the same time, the tortuous path E permits efficient entrance and exit of sterilant between the test microorganisms and the surrounding environment.

A microporous, preferably hydrophilic, membrane G is positioned within the cap C in the tortuous path E between the environment and the biological indicator. The microporous membrane covers and encloses a cavity (not shown) within the biological indicator housing assembly B.

Membrane G performs at least two functions. The first function is to prohibit any of the test microorganisms from moving out of the biological indicator housing assembly B. The second function is to allow entrance of the sterilant into the housing assembly B in contact with the test microorganisms, and removal of the sterilant from the housing assembly B. This allows a secure storage of the test microorganisms within the biological indicator housing assembly B while testing the effectiveness of a sterilization process.

The effectiveness of the sterilization process may be tested by contacting the test microorganisms with the sterilant in the same manner as the load being sterilized. The sterilant flows along the tortuous path E to biological indicator housing assembly B where the sterilant flows over and among the test microorganisms. After completion of a sterilization process, assay medium housing D is compressed into the cap C. This compression simultaneously introduces the test microorganisms into the assay medium F and closes off the tortuous path E. This closing off of the tortuous path seals off the test microorganisms from the environment.

Figure 6:
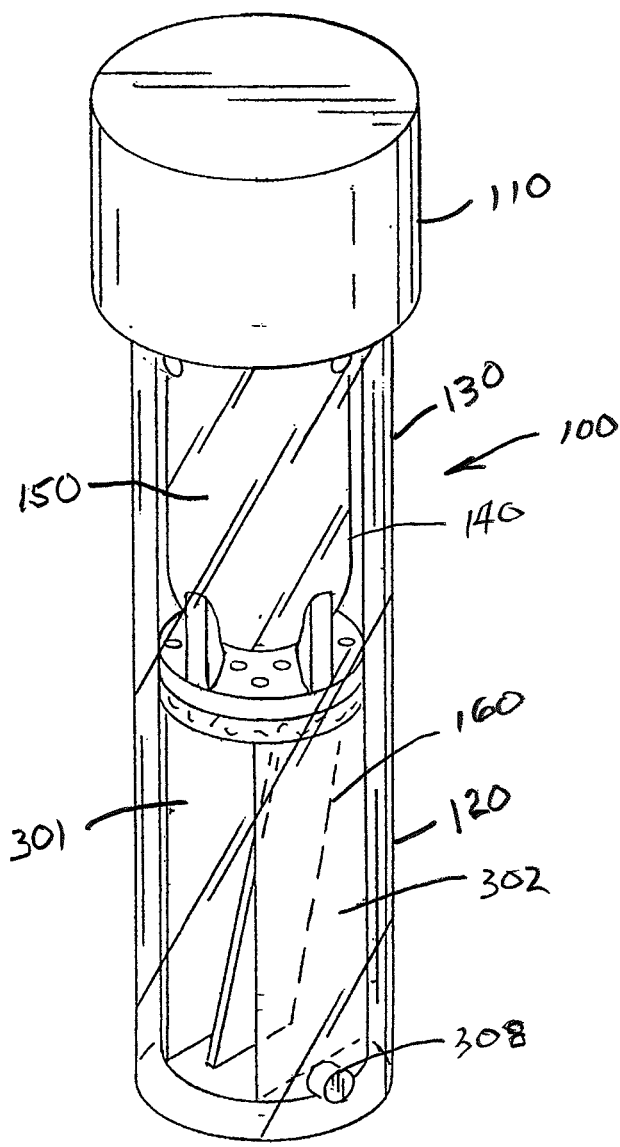
FIG. 6 is a perspective view of a capacitance device which can be used in accordance with the present invention.
Figure 7:
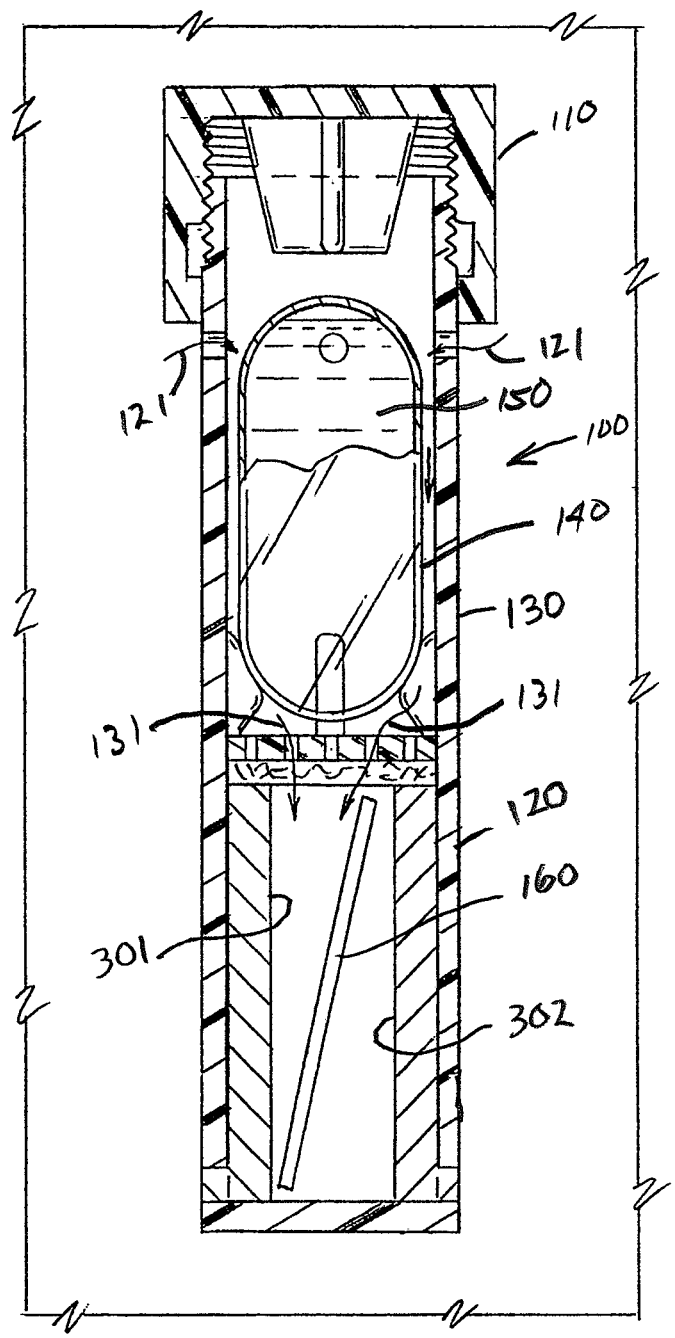
FIG. 7 is a cross-sectional view of the capacitance device of FIG. 6 showing a cap mounted on the capacitor in a first non-activated position.
Figure 8:
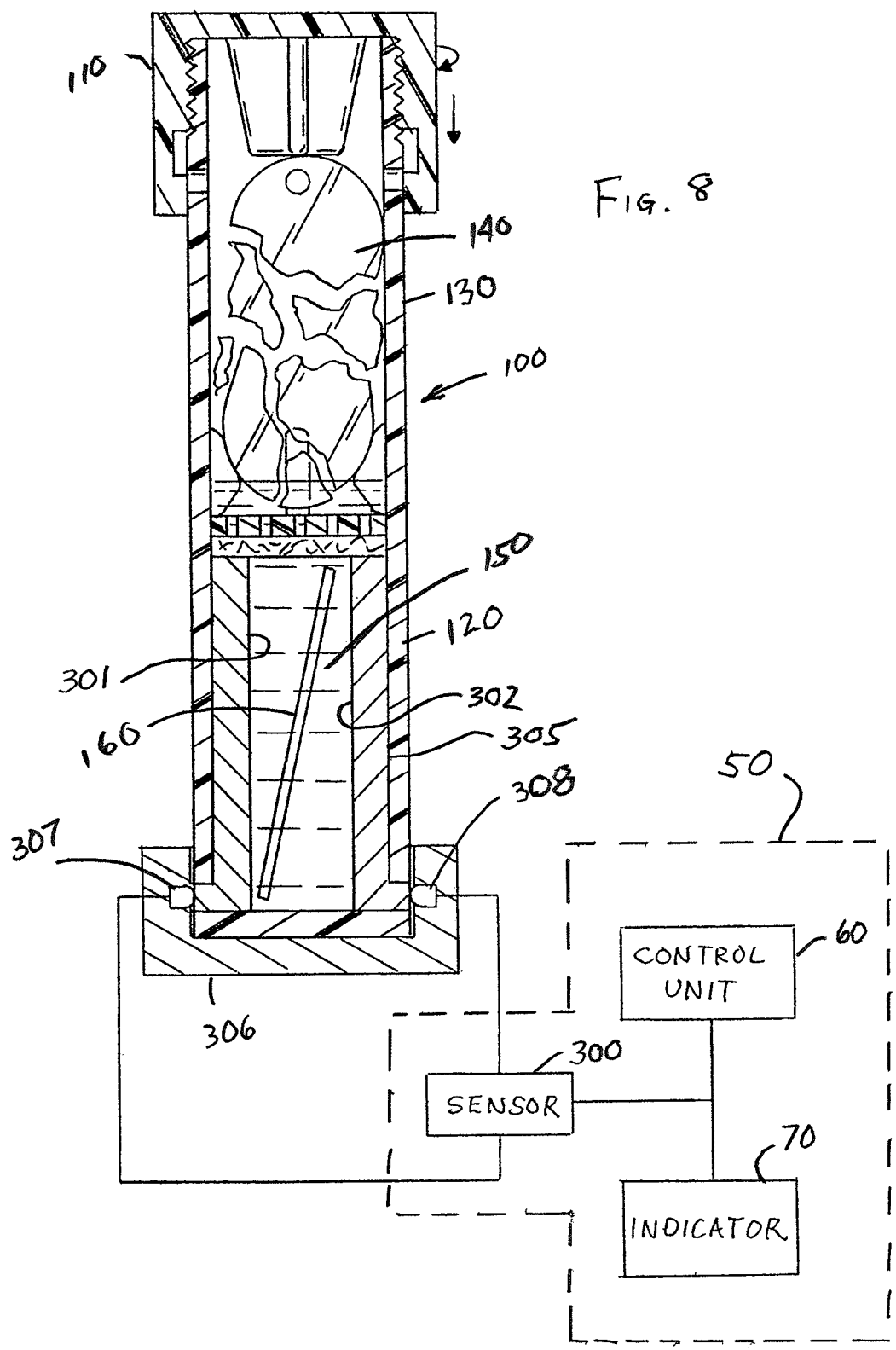
FIG. 8 is a cross-sectional view of the capacitance device of FIG. 6 showing the cap mounted on the capacitor in a second activated position, the capacitor being configured with a sensing apparatus according to an embodiment of the present invention.

In an embodiment, the capacitance device illustrated in FIGS. 6-8 may be used. Referring to FIGS. 6-8, capacitance device 100 includes cap 110, first compartment 120 and second compartment 130. First compartment 120 holds biological indicator 160, and contains electrical conductors 301 and 302. The biological indicator 160 comprises test microorganisms (e.g., spores) on a carrier. Second compartment 130 holds frangible ampoule 140 which contains assay medium 150. The frangible ampoule 140 may be a glass ampoule.

When used in a sterilization process, the cap 110 is held in an open position as illustrated in FIG. 7. The capacitance device 100 and items to be sterilized are then subjected to the sterilization process. During the sterilization process, the sterilant flows through openings between the cap 110 and the second compartment 130, as indicated by arrows 121, and then into the first compartment 120, as indicated by arrows 131, where it contacts and acts upon the test microorganisms on the biological indicator 160.

After the sterilization process is complete, the capacitance device 100 is activated by screwing the cap 110 downward into a closed position as shown in FIG. 8. This results in the frangible ampoule 140 being broken. Assay medium 150 then flows from the second compartment 130 into the first compartment 120 and contacts the biological indicator 160. The combination of the biological indicator 160 and the assay medium 150 forms a dielectric positioned between the conductors 301 and 302. The capacitance device 100 is then placed in dock 306 which contains electrical contacts 307 and 308. The electrical contacts 307 and 308 contact electrical conductors 301 and 302, respectively.

Sensing apparatus 50 is comprised of control unit 60, indicator 70, and sensor 300. A power source (e.g., a battery), which is not shown, provides power to control unit 60, indicator 70 and sensor 300. Control unit 60 may be a microprocessor or a microcontroller. Control unit 60 may also include (or is connected with) a data storage device for storing data. Indicator 70 may take the form of a visual and/or an audible indicator. These may include one or more LEDs, LCDs, speakers, and/or alarms.

Figure 2:
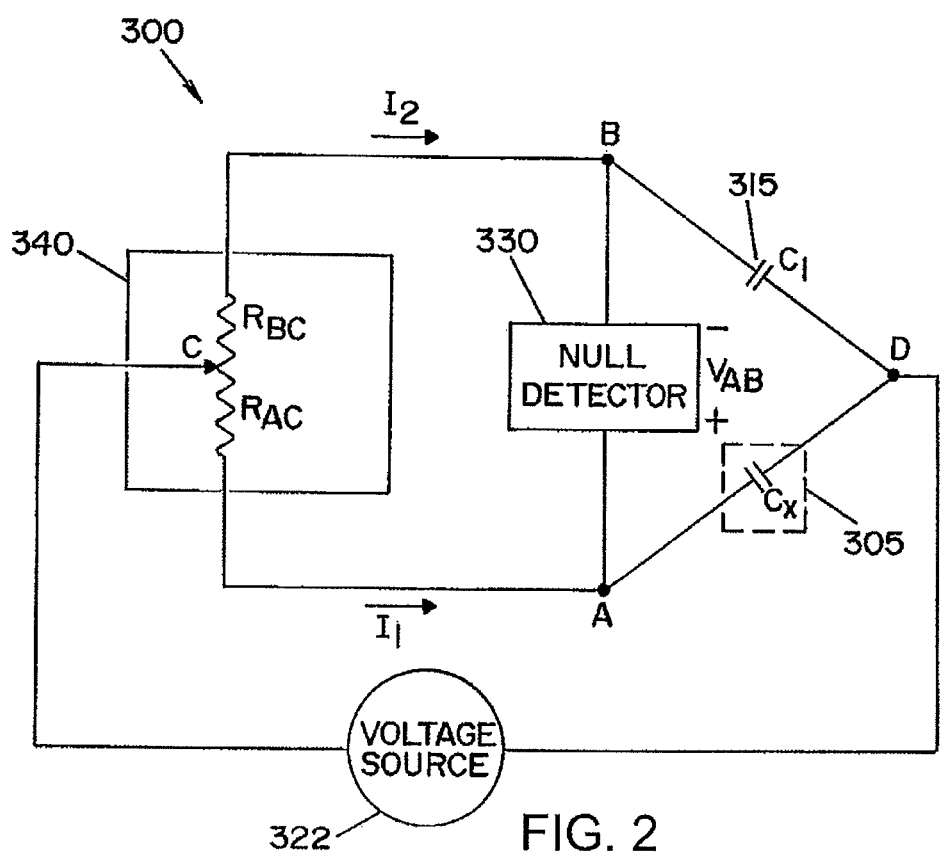
FIG. 2 is a schematic diagram of an exemplary capacitive sensor for determining the efficacy of a sterilization process, according to an embodiment.

Referring to FIG. 2, sensor 300 includes a capacitor 305 that acts as a sensing element. Capacitor 305 is comprised of a pair of electrical conductors 301 and 302 located within assay medium housing D of capacitance device A, or within first compartment 120 of capacitance device 100. In capacitance device A, the assay medium F is located between electrical conductors 301 and 302. Assay medium F in combination with test microorganisms introduced into assay medium housing D act as a dielectric for capacitor 305. In capacitance device 100, the assay medium 150 flows into first compartment 120, and the combination of the assay medium 150 and the biological indicator 160 function as a dielectric between the electrical conductors 301 and 302.

Electrical properties of the capacitor are responsive to the physical condition of the test microorganisms (i.e., live vs. dead) that contact the assay medium after the sterilization process in completed. In this respect, live spores, for example, tend to be spheroidal in nature, whereas dead spores tend to be similar in morphology to deflated balloons. The electrical properties of the capacitor are measurably different with the presence of live test microorganisms than with the presence of dead test microorganisms, since the dielectric constant of the assay medium combined with live test microorganisms differs from the dielectric constant of the assay medium combined with dead test microorganisms. As a result of these different dielectric constants, the capacitance of the capacitor is measurably different with assay medium combined with live test microorganisms, as compared to assay medium combined with dead test microorganisms. By observing these differences in capacitance, it can be determined whether a sterilization process has been effective.

While not wishing to be bound by theory, it is believed that as the test microorganisms die, ions are emitted and the emission of these ions is, in part, what is producing the difference in the observed capacitance measurements. Live and dead test microorganisms express significantly different capacitances that do not require signal accumulation time or growth promotion incubation in order to be detected. As such, with the present invention it is possible to obtain an instantaneous read on whether a sterilization process has been successful by measuring the capacitance of the biological indicator at the conclusion of the sterilization process.

Sensor 300 is in the form of a "bridge circuit." The bridge circuit may be used to determine the value of an unknown impedance in terms of other impedances of known value. Highly accurate measurements are possible because a null condition is used to determine the unknown impedance. The bridge circuit is used to determine the presence of live or dead spores inside media housing D (FIG. 1) or in first compartment 120 (FIGS. 6-8) between electrical conductors 301 and 302.

Sensor 300 is comprised of a voltage source 322, a null detector 330, an electronic potentiometer 340, a capacitor 315 of a known capacitance $C_1$, and capacitor 305 having a capacitance $C_x$. Capacitance $C_x$ of capacitor 305 will vary in response to the presence of live or dead test microorganisms (e.g., spores) inside assay media housing D (FIG. 1) or in first compartment 120 (FIGS. 6-8).

In an embodiment, the inventive capacitor may be a parallel plate capacitor. However, it should be appreciated that the capacitor may be constructed in a different form, including, but not limited to, a cylindrical or spherical-shaped capacitor. If a spherical capacitor is used as the capacitor, holes may be placed in the outer shell of the capacitor such that the test microorganisms may enter and exit the capacitor. The electrical conductors may be made of copper, aluminum, silver, gold, platinum, or a combination of two or more thereof. The electrical conductors may comprise indium tin oxide (ITO) on glass.

Electronic potentiometer 340 functions in the same manner as a mechanical potentiometer. In this regard, electronic potentiometer 340 may be a three terminal device. Between two of the terminals is a resistive element. The third terminal known as the "wiper" may be connected to various points along the resistive element. In the illustrated embodiment, the wiper is digitally controlled by control unit 60. The wiper divides the resistive element into two resistors $R_{BC}$ and $R_{AC}$. Electronic potentiometer 340 may take the form of a digitally programmable potentiometer (DPP™) available from Catalyst Semiconductor, Inc. of Sunnyvale, Calif.

In an embodiment, voltage source 322 provides an AC voltage signal, such as a sinusoidal or pulse waveform. Null detector 330 is a device for detecting a null condition (i.e., a short circuit), such as a galvanometer, a voltmeter, a frequency-selective amplifier, and the like.

Operation of sensor 300 will now be described with reference to FIG. 2. The elements of the bridge circuit are connected between junctions AC, BC, AD, and BD. Electronic potentiometer 340 is operated by control unit 60 to vary the resistances $R_{BC}$ and $R_{AC}$ until the potential difference between junctions A and B ($V_{AB}$) is zero. When this situation exists, the bridge is said to be balanced or is "nulled." The following relationships then hold for voltages in the main branches:

$$V_{AC}=V_{BC}, \text{ and } V_{AD}=V_{BD},$$

where $V_{AC}$ is the voltage between junctions A and C, $V_{BC}$ is the voltage between junctions B and C, $V_{AD}$ is the voltage between junctions A and D, and $V_{BD}$ is the voltage between junctions B and D. Accordingly, $$V_{AD}/V_{AC}=V_{BD}/V_{BC}$$

$$V_{AD}=V_{BD}/(V_{AC}/V_{BC})$$

Capacitor 305 of capacitance $C_x$ is connected between junctions A and D, and capacitor 315 of known capacitance $C_1$ is connected between junctions B and D. Electronic potentiometer 340, connected from junction A to junction C to junction B, is adjusted by control unit 60 to vary the voltages $V_{AC}$ and $V_{BC}$.

When a null is detected by null detector 330, current $I_1$ flows from junction C to junction A to junction D, and a current $I_2$ flows from junction C to junction B to junction D. The voltage $V_{AC}$ across junctions A to C, and the voltage $V_{BC}$ across junctions B to C are:

$$V_{AC}=I_1 R_{AC} \text{ and } V_{BC}=I_2 R_{BC}.$$

The voltage across a capacitor with capacitance C, current I, and frequency f is:

$$V = \frac{I}{2\pi f C}$$

Therefore, the voltages $V_{AD}$ and $V_{BD}$ may be expressed as:

$$V_{AD} = \frac{I_1}{2\pi f C_x}$$

$$V_{BD} = \frac{I_2}{2\pi f C_1}$$

As discussed above, $V_{AD}=V_{BD}/(V_{AC}/V_{BC})$, $V_{AC}=I_1 R_{AC}$, and $V_{BC}=I_2 R_{BC}$. Therefore, $$C_x = C_1 \left( \frac{R_{BC}}{R_{AC}} \right).$$

In view of the forgoing relationship, when a null condition is detected, the resistance values for $R_{BC}$ and $R_{AC}$, along with the known capacitance $C_1$ of capacitor 315, can be used to determine the unknown value of capacitance $C_x$ of capacitor 305.

By configuring capacitor 305 as an element of a bridge circuit, a measure of resistance values $R_{AC}$ and $R_{BC}$, when the bridge is balanced or nulled, can be used to determine the capacitance $C_x$ of capacitor 305. Changes to the capacitance $C_x$ of capacitor 305 is indicative of the presence of live or dead spores in assay media F.

For a parallel plate capacitor, $C=(k\varepsilon_0)(A/d)=(\varepsilon)(A/d)$, where C is capacitance, k is the dielectric constant, $\varepsilon_0$ is the permittivity of free space ($8.85 \times 10^{-12}$ F/m), $\varepsilon$ is the permittivity (Farads/meter) of the capacitor dielectric, A is the area of the capacitor plates (m$^2$), and d is the separation in meters between the capacitor plates. As $\varepsilon$ increases, the capacitance C will increase. Where the capacitor is a parallel plate capacitor with circular plates of diameter D, $$C=(\pi D^2 \varepsilon)/(4d).$$

The dielectric constant k of the capacitor can be determined according to the following expression:

$$k = \frac{4dC}{\pi D^2 \varepsilon_0},$$

where the value of capacitance, C, is determined as discussed above. The dielectric constant of the capacitor can also be determined by determining the capacitance with the dielectric in place between the conducting plates ($C_d$), and then determining the capacitance without the dielectric in place ($C_o$). The ratio of the two capacitances equals the dielectric constant, $$k = \frac{C_d}{C_0}.$$

The response of a capacitor is influenced by the characteristics (e.g., frequency) of the AC waveform applied thereto. In this regard, capacitive reactance ($X_c$) is a function of frequency. Capacitive reactance is the opposition offered to the flow of alternating current by pure capacitance, and is expressed in ohms ($X_c=1/(2\pi fC)$). Accordingly, frequency of the waveform generated by voltage source 322 influences the response of capacitors.

Figure 3:
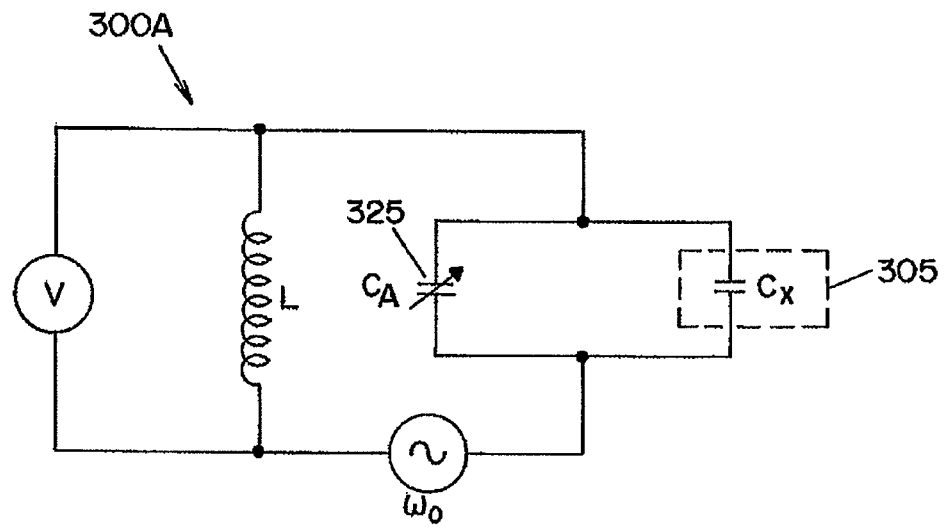
FIG. 3 is a schematic diagram illustrating an exemplary capacitive sensor for determining the efficacy of a sterilization process, according to another embodiment.

While sensor 300 is shown as being in the form of a bridge circuit, other types of circuits and techniques (including other types of bridge circuits, and capacitance meters) may be used to measure capacitance. For example, FIG. 3 illustrates an alternative sensor 300A. Sensor 300A is an LC resonant circuit, including a variable capacitor 325 (having a capacitance $C_A$), and capacitor 305 (having a capacitance $C_x$) that acts as the sensing element, as described above. Since the resonance frequency $\omega_0 = [L(C_A+C_x)]^{-1/2}$, the unknown capacitance $C_x$ of capacitor 305 can be determined.

Figure 4:
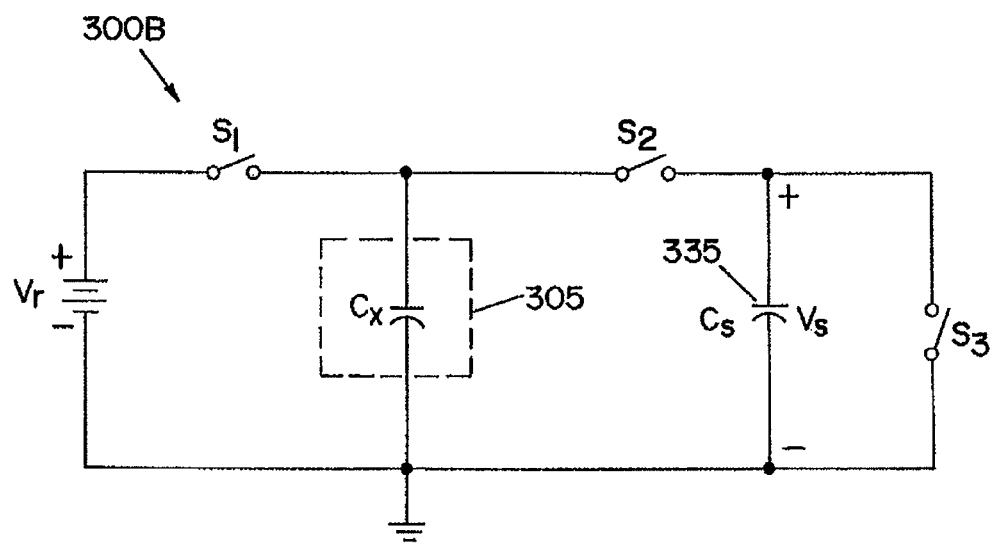
FIG. 4 is a schematic diagram of an exemplary capacitive sensor for determining the efficacy of a sterilization process, according to another embodiment.

FIG. 4 illustrates yet another alternative sensor 300B suitable for use in connection with the present invention. Sensor 300B is a "charge transfer" sensor circuit. Charge transfer sensor circuits are recognized to provide resolutions of fractions of a femtoFarad. In a charge transfer sensor circuit the unknown capacitance $C_x$ of a sense electrode is determined by charging the sense electrode to a fixed potential, and then transferring that charge to a charge detector comprising a capacitor 335 of known capacitance $C_s$. In sensor 300B, capacitor 305 of unknown capacitance $C_x$ acts as a sensing element, as described above. In this regard, an assay medium and spores fill the gap between the conducting plates of capacitor 305, thereby acting as an insulator or "dielectric" of capacitor 305. Capacitor 305 is first connected to a DC reference voltage ($V_r$) via a switch $S_1$. Switch $S_1$ is reopened after capacitor 305 is satisfactorily charged to the potential of $V_r$. Then, after as brief as possible a delay so as to minimize leakage effects caused by conductance, switch $S_2$ is closed and the charge (Q) present on capacitor 305 is transferred to capacitor 335 (i.e., the charge detector). Once the charge Q is satisfactorily transferred to capacitor 335, switch $S_2$ is reopened. By reading voltage $V_s$, the capacitance $C_x$ of capacitor 305 can be determined. $V_s$ may be input to an amplifier to provide the scaling necessary to present an analog-to-digital converter (ADC) with a useful range of voltage for digital processing. Switch $S_3$ acts as a reset means to reset the charge between charge transfer cycles, so that each charge transfer cycle has a consistent initial condition. Switches $S_1$, $S_2$ and $S_3$ may be electromechanical switches or transistors. Preferably, digital control logic is used to control switches $S_1$, $S_2$ and $S_3$. Capacitor 335 may be significantly larger than capacitor 305.

The equations governing sensor 300B are as follows:

$V_s = V_r[C_y/(C_y+C_s)]$, therefore $C_y = V_s C_s/[V_r-V_s]$.

The charge-transfer sensor has been applied in a self-contained capacitance-to-digital-converter (CDC) integrated circuit (IC). For example, Quantum Research Group produces a QProx™ CDC sensor IC (e.g., QT300 and QT301 CDC sensor ICs) for detecting femtofarad level changes in capacitance. The CDC sensor IC outputs a digital value corresponding to the detected input capacitance. The value of an external sampling capacitor controls the gain of the sensor.

Other high sensitivity circuitry is provided by such devices that may be used include the PTL 110 capacitance transducer from Process Tomography Limited of Cheshire, United Kingdom. The PTL 110 measures small values of capacitance (up to 10 pF) with a resolution of 1 fF. A 7600 Plus Precision LCR Meter Capacitance Bridge from IET Labs, Inc. of Westbury, N.Y., allows for measurement of capacitances in the range from 0.01 fF to 10 F. Tektronix produces the Tektronix 130 LC Meter that measures capacitance from 0.3 pF to 3 pF. It has also been acknowledged in the prior art literature that capacitance sensor circuits using modern operational amplifiers and analog-to-digital converters (ADCs) can easily obtain resolutions to 0.01 pF. In an embodiment, a dielectric cell may be used to provide a more accurate capacitance reading by screening out extraneous electrical signals; see, ASTM D150.

Operation of the present invention, as illustrated in FIG. 1, will now be summarized. The capacitance device A is located within an enclosure containing at least one item to be sterilized. The test microorganisms in the hosing assembly B along with the item to be sterilized are then exposed to a sterilant for an effective period of time to provide for sterilization. During the sterilization process the test microorganisms are maintained within the housing assembly B as illustrated in FIG. 1. After the sterilization process is completed, the test microorganisms are combined with the assay medium F. The assay medium, combined with the test microorganisms, is placed between electrical conductors 301 and 302 to form a dielectric. Sensing apparatus 50 determines a measured capacitance of the capacitor to ascertain whether the test microorganisms are alive or dead.

In accordance with an embodiment of the present invention, a method for determining the efficacy of a sterilization process, includes the steps of: (a) placing a biological indicator comprising test microorganisms within a region containing at least one item to be sterilized; (b) exposing the at least one item and the biological indicator to a sterilant; (c) after exposure to the sterilant, placing the biological indicator and an assay medium between a pair of electrical conductors of a capacitor, wherein the biological indicator and the assay medium serve as a dielectric for the capacitor; (d) measuring the capacitance of the capacitor; and (e) determining whether the measured capacitance values indicate the presence of live test microorganisms. The capacitance values may be used to count the live test microorganisms, if any, that survive the sterilization process. The determination of whether live test microorganisms are present, and if so, how many, can be accomplished instantaneously, or within a period of time of up to about 2,000 seconds, or up to about 1500 seconds, or up to about 1000 seconds, or up to about 500 seconds, or up to about 200 seconds, or up to about 100 seconds, or up to about 50 seconds, or up to about 30 seconds, or in the range from about 5 to about 2000 seconds, or from about 10 to about 1800 seconds, or from about 20 to about 1500 seconds, or from about 30 to about 1200 seconds, or from about 50 to about 1000 seconds, or from about 60 to about 800 seconds, or from about 100 to about 600 seconds, or from about 200 to about 600 seconds, or from about 300 to about 600 seconds.

A control capacitance value may be determined in advance and pre-stored in a memory of control unit 60. The control capacitance value may be dependent upon several factors, including the type of assay medium, number of test microorganisms, physical configuration of the capacitor (e.g., dimensions and shape of the capacitor plates), etc.

Indicator 70 may be used to provide a visual and/or audible indication of whether viable test microorganisms are detected. For instance, a green LED may be illuminated to indicate the absence of viable test microorganisms (i.e., a successful sterilization cycle), while a red LED may be illuminated to indicate the presence of viable test microorganisms (i.e., an unsuccessful sterilization cycle). Alternatively, an audible alarm may be activated when it is determined that viable test microorganisms are present.

Example 1

A Keysight Technologies model U1701B Handheld Capacitance Meter with measurement range from 0.1 pF to 199.99 mF is used to test two sets of spore test strips. One set of spore test strips (treated) is subjected to a steam sterilization process, and the other set (untreated) is not subjected to the sterilization process. The Keysight capacitance meter is electrically connected to a Bio-Rad Shock Pod. The Bio-Rad Shock Pod provides electrical communication with a Mirus Ingenio 0.2 cm cuvette. The cuvette is a disposable plastic container that is 4.5 cm tall (without its cap) and 1.2 cm on each side. The sidewalls of each of two opposing sides of the cuvette are constructed of aluminum plates (each being 2 cm tall and 1 cm wide). The aluminum plates extend through the walls and communicate with the interior of the cuvette. The aluminum plates function as electrical conductors. The gap between the plates inside the cuvette is 0.2 cm.

The test strips are VERIFY® Spore Test Strips for 540® Sterilant Concentrate supplied by STERIS Corporation. These test strips are cellulose strips that are 0.6 cm wide, 3.8 cm long, and less than 0.1 cm thick. These test strips are characterized by a population of *Geobacillus stearothermophilus* spores of approximately $10^6$ spores. One of each of these test strips is folded over so that it is 1.9 cm long. The test strips are inserted into the cuvette, and positioned between the aluminum plates. A 20% glycerol (v/v in water) solution is added to the cuvette to cover the tops of the plates, thus filling all voids. The test strip in combination with the glycerol solution form a dielectric. The aluminum plates function as electrical conductors. The capacitance of each test strip is determined by applying an electrical signal to the conductors and measuring capacitance using the Keysight capacitance meter.

An additional sample of each test strip (treated and untreated) is transferred to a growth medium to confirm the state of the spores strips. The spores on the untreated test strip grow overnight, while the spores on the treated test strip do not grow. This indicates a complete spore kill for the treated test strip, i.e., a successful sterilization.

Figure 5:
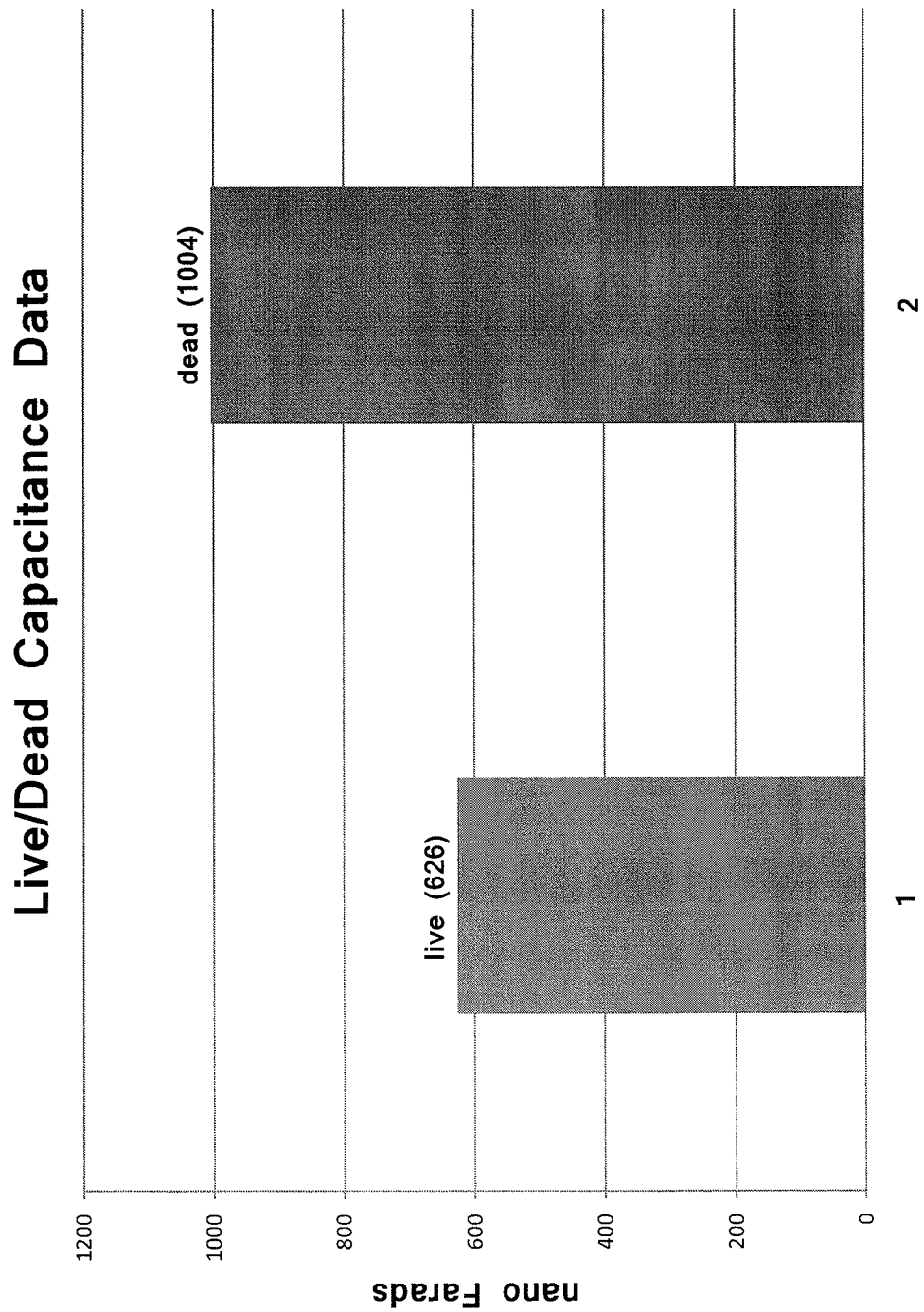
FIG. 5 is a bar graph showing capacitance levels obtained in Example 1.

The treated test strip shows a capacitance level of 1004 nanofarads (nF), with a standard deviation of 33 nF. The untreated test strip shows a capacitance level of 626 nF, with a standard deviation of 23 nF. These results are shown in FIG. 5.

Example 2

The capacitance value at one standard deviation for the untreated test strip (live spores) in Example 1 is: 626 nF+23 nF=649 nF to 626 nF−23 nF=603 nF. The capacitance value at one standard deviation for the treated test strip (dead spores) in Example 1 is: 1004−33=971 nF to 1004+33 nF=1037 nF. For purposes of this example, it is assumed that the spore population for the test strip is $10^6$ spores. To determine the smallest accuracy level needed for the capacitor to detect one live spore, the following difference in capacitance levels is determined: 971 nF−649 nF (the smallest value for $10^6$ dead spores minus the largest value for $10^6$ live spores)=322 nF. This number is then divided by $10^6$ spores to yield 0.32 pF/spore (or about 0.3 pF/spore). This indicates that in using a capacitance bridge with an accuracy of less than about 0.3 pF, it is possible to detect one live spore out of $10^6$ spores. If no live spores can be detected, then all of the spores are dead and the sterilization process is successful.

Example 3

The software for an Andeen-Hagerling AH 2700A capacitance bridge is used to calculate capacitance levels for counting sores. The resolution of the AH 2700A bridge is 0.8 aF. Since as indicated in Example 2 a change of 0.3 pF/spore is required to detect the presence of live spores, the level of resolution of 0.8 aF is 375 times better than needed: 0.3 pF/0.8 aF=375. The accuracy of the AH 2700A bridge is 5 ppm or 5E (−6). If it is assumed that this accuracy is based on the largest value the AH 2700A bridge can measure (1.5 microfarads), the accuracy is 5E(−6)×1.5E(−6)=7.5E(−12) =7.5 pF. However, as indicated above, an accuracy of 0.3 pF is needed to indicate the presence of one live spore. At an accuracy of 7.5 pF, it is possible to show a capacitance change that translates to 25 live sores ((7.5 pF)(0.3 pF/spore) =25 spores).

Using software provided for the AH2700A bridge, the capacitance level that would be required to provide an accuracy level of less than 0.3 pF is determined to be 15 nF or less. This indicates that it is possible to provide a capacitor that can detect one live spore on a treated test strip that initially contains $10^6$ live spores prior to sterilization. The values from the AH2700A software that demonstrate this are as follows:

| Capacitance | Accuracy in PPM | Accuracy in Farads | Maximum Number of Spores |
|---|---|---|---|
| 1004 nf | 68.1 | (1004 nf)(68.1E−6) = 68.4 pF | (68.4 pF)/(0.3 pF/spore) = 228 spores |
| 500 nF | 46.5 | (500 nF)(46.5E−6) = 23.25 pF | (23.25 pF)/0.3 pF/spore) = 77.5 spores |
| 60 nF | 35.2 | (60 nF)(35.2E−6) = 2.1 pF | (2.1 pF)/(0.3 pF/spore) = 7 spores |
| 40 nF | 25.2 | 1 pF | 4 spores |
| 20 nF | 25.1 | 0.5 pF | 2 spores |
| 15 nF | 15.1 | 0.23 pF | 1 spore |
| 10 nF | 15.1 | 0.15 pF | 0 spores |

Example 4

The procedure used in Example 1 is repeated except that the test strip is an untreated test strip that contains *Bacillus atrophaeus* spores. This is compared to a blank cellulose strip. The untreated test strip shows a capacitance level of 609.2 nF. The blank cellulose strip shows a capacitance of 1042.7 nF.

Example 5

A statistical analysis is conducted using the test strips shown in Example 1 to determine whether there is a statistical difference in capacitance levels for the treated and the untreated test strips. Two cuvettes (one for a treated test strip, and one for an untreated test strip) are separately placed in the Bio-Rad Shock Pod and the Keysight capacitance meter is activated. With each test strip, an initial capacitance reading is taken, and then readings are taken every 5 seconds for 15 minutes (180 readings). At the conclusion of the first 15 minute trial (180 data points), the data are collected. The results for this first trial are reported in the tables below as "live 1" (first trial, untreated spore strip) and "dead 1" (first trial, treated spore strip). The capacitance meter is then activated for a second trial, and then a third trial, with each trial consisting of readings taken every 5 seconds for 15 minutes (180 readings). The results for the second and third trials are reported in the tables below as follows: "live 2" (second trial, untreated spore strip); "dead 2" (second trial, treated spore strip); "live 3" (third trial, untreated spore strip); and "dead 3" (third trial, treated spore strip). The data for the three trials are also combined (540 readings), and reported below as "all live" (first, second and third trials combined, untreated spore strip), and "all dead" (first, second and third trials, treated spore strip). The numerical values shown below are capacitance levels measured in nanofarads (nF).

The analysis that is used can be referred to as a Two-Sample T-Test which determines whether the means of two independent populations are equal to a target value. In the data provided below, "N" is the number of readings or data points (180 for each analysis, except for the last analysis where all data points from the treated and the untreated spores strips are shown and N is 540). The term "Mean"

refers to the sum of the capacitance levels measured in nF divided by the number (N) of data points. The term "St Dev" refers to standard deviation, which is a measure of the variability of the capacitance levels within a single sample. The term "SE Mean" refers to the standard error of the mean which is a measure of the variability of the capacitance levels between samples. The term "Difference=$\mu$ (live_)−$\mu$ (dead_)" refers to the difference between the means of the live test with the dead test. The term "Estimate for difference" refers to an estimated difference between the two means based upon spore population statistics. The term "95% CI for difference" refers to the bounds of the 95% confidence interval, if the set includes 0 the sample set means would be considered equivalent. The term "T-Test of difference" refers to a hypothesis for test that both means are equivalent (T=0). The term "T-Value" refers to the calculated t-test value for comparison to T=0. The term "P-Value" refers to the value normally used for determination of equivalence. The confidence interval used here is 95%, therefore, any value above 0.05 for the P-value indicates the spore population means are equivalent. The term "DF" refers to degrees of freedom in the test.

The results are indicated below:

|  | N | Mean | StDev | SE Mean |
|---|---|---|---|---|
| (A) live 1, dead 1 | | | | |
| live 1 | 180 | 579 | 129 | 9.6 |
| dead 1 | 180 | 931 | 206 | 15 |
| Difference = $\mu$ (live 1) − $\mu$ (dead 1) | | | | |
| Estimate for difference: −351.9 | | | | |
| 95% CI for difference: (−387.7, −316.2) | | | | |
| T-Test of difference = 0 (vs ≠): T-Value = −19.38 P-Value = 0.000 | | | | |
| DF = 301 | | | | |
| (B) live 1, dead 2 | | | | |
| live 1 | 180 | 579 | 129 | 9.6 |
| dead 2 | 180 | 876 | 185 | 14 |
| Difference = $\mu$ (live 1) − $\mu$ (dead 2) | | | | |
| Estimate for difference: −296.3 | | | | |
| 95% CI for difference: (−329.5, −263.2) | | | | |
| T-Test of difference = 0 (vs ≠): T-Value = −17.59 P-Value = 0.000 | | | | |
| DF = 320 | | | | |
| (C) live 1, dead 3 | | | | |
| live 1 | 180 | 579 | 129 | 9.6 |
| dead 3 | 180 | 911 | 176 | 13 |
| Difference = $\mu$ (live 1) − $\mu$ (dead 3) | | | | |
| Estimate for difference: −331.3 | | | | |
| 95% CI for difference: (−363.4, −299.2) | | | | |
| T-Test of difference = 0 (vs ≠): T-Value = −20.32 P-Value = 0.000 | | | | |
| DF = 328 | | | | |
| (D) live 2, dead 3 | | | | |
| live 2 | 180 | 577 | 110 | 8.2 |
| dead 3 | 180 | 911 | 176 | 13 |
| Difference = $\mu$ (live 2) − $\mu$ (dead 3) | | | | |
| Estimate for difference: −333.5 | | | | |
| 95% CI for difference: (−363.9, −303.0) | | | | |
| T-Test of difference = 0 (vs ≠): T-Value = −21.54 P-Value = 0.000 | | | | |
| DF = 299 | | | | |
| (E) live 2, dead 2 | | | | |
| live 2 | 180 | 577 | 110 | 8.2 |
| dead 2 | 180 | 876 | 185 | 14 |
| Difference = $\mu$ (live 2) − $\mu$ (dead 2) | | | | |
| Estimate for difference: −298.5 | | | | |
| 95% CI for difference: (−330.1, −266.9) | | | | |
| T-Test of difference = 0 (vs ≠): T-Value = −18.59 P-Value = 0.000 | | | | |
| DF = 291 | | | | |
| (F) live 2, dead 1 | | | | |
| live 2 | 180 | 577 | 110 | 8.2 |
| dead 1 | 180 | 931 | 206 | 15 |
| Difference = $\mu$ (live 2) − $\mu$ (dead 1) | | | | |
| Estimate for difference: −354.1 | | | | |
| 95% CI for difference: (−388.4, −319.8) | | | | |
| T-Test of difference = 0 (vs ≠): T-Value = −20.32 P-Value = 0.000 | | | | |
| DF = 272 | | | | |
| (G) live 3, dead 1 | | | | |
| live 3 | 180 | 72 | 104 | 7.8 |
| dead 1 | 180 | 31 | 206 | 15 |
| Difference = $\mu$ (live 3) − $\mu$ (dead 1) | | | | |
| Estimate for difference: −359.5 | | | | |
| 95% CI for difference: (−393.5, −325.6) | | | | |
| T-Test of difference = 0 (vs ≠): T-Value = −20.86 P-Value = 0.000 | | | | |
| DF = 265 | | | | |
| (H) live 3, dead 2 | | | | |
| live 3 | 180 | 572 | 104 | 7.8 |
| dead 2 | 180 | 876 | 185 | 14 |
| Difference = $\mu$ (live 3) − $\mu$ (dead 2) | | | | |
| Estimate for difference: −303.9 | | | | |
| 95% CI for difference: (−335.2, −272.7) | | | | |
| T-Test of difference = 0 (vs ≠): T-Value = −19.17 P-Value = 0.000 | | | | |
| DF = 282 | | | | |
| (I) live 3, dead 3 | | | | |
| live 3 | 180 | 572 | 104 | 7.8 |
| dead 3 | 180 | 911 | 176 | 13 |
| Difference = $\mu$ (live 3) − $\mu$ (dead 3) | | | | |
| Estimate for difference: −338.9 | | | | |
| 95% CI for difference: (−369.0, −308.9) | | | | |
| T-Test of difference = 0 (vs ≠): T-Value = −22.19 P-Value = 0.000 | | | | |
| DF = 290 | | | | |
| (J) all live, all dead | | | | |
| All live | 540 | 576 | 115 | 4.9 |
| All dead | 540 | 906 | 191 | 8.2 |
| Difference = $\mu$ (all live) − $\mu$ (all dead) | | | | |
| Estimate for difference: −329.78 | | | | |
| 95% CI for difference: (−348.59, −310.97) | | | | |
| T-Test of difference = 0 (vs ≠): T-Value = −34.41 P-Value = 0.000 | | | | |
| DF = 884 | | | | |

These test results indicate that, with a 95% confidence level, there is a statistical difference between the capacitance levels for the spore strips with live spores (untreated) compared to the spore strips with dead spores (treated).

While the invention has been explained in relation to various embodiments, it is to be understood that various modifications thereof will become apparent to those skilled in the art upon reading the specification. Therefore, it is to be understood that the invention disclosed herein includes any such modifications that may fall within the scope of the appended claims.

The invention claimed is:

1. A capacitance device for testing the efficacy of a sterilization process, comprising:
a first compartment containing a biological indicator, the biological indicator comprising a spore strip, the spore strip comprising a plurality of the spores on a carrier, the carrier being a cellulose strip, the first compartment containing two capacitor plates separated by a gap, the separation provided by the gap being in the range from about 0.5 to about 5 mm, the biological indicator being positioned in the gap between the capacitor plates, the first compartment being adapted to permit a sterilant to be brought into contact with the biological indicator during the sterilization process; and
a second compartment containing a liquid assay medium, the liquid assay medium being a glycerol in water solution, the second compartment being adapted to maintain the liquid assay medium separate from the biological indicator during the sterilization process, and the second compartment being adapted to permit the liquid assay medium to flow into the gap between the capacitor plates in contact with the biological indicator and the capacitor plates after the biological indicator has been exposed to the sterilant, the biological indicator and the liquid assay medium forming a dielectric between the capacitor plates, the dielectric being an electrical insulator that is polarized when subjected to an applied electrical field, when the dielectric is subjected to the applied electrical field electrical charges do not flow through the dielectric but only shift from their average equilibrium positions; and a capacitance bridge for detecting capacitance levels and determining the efficacy of the sterilization process within a period of time of up to about 2000 seconds by determining whether the spores on the carrier are alive or dead based on the capacitance levels, the capacitance bridge having an accuracy level of about 1 µF or less.

2. The capacitance device of claim 1 wherein the spores comprise spores of the *Bacillus* or Clostridia genera.

3. The capacitance device of claim 1 wherein the spores comprise spores of *Geobacillus stearothermophilus, Bacillus atrophaeus, Bacillus sphaericus, Bacillus anthracis, Bacillus pumilus, Bacillus coagulans, Clostridium sporogenes, Clostridium difficile, Clostridium botulinum, Bacillus subtilis globigii, Bacillus cereus, Bacillus circulans*, or a mixture of two or more thereof.

4. The capacitance device of claim 1 wherein the spores comprise *Geobacillus stearothermophilus* spores, *Bacillus atrophaeus* spores, or a mixture thereof.

5. The capacitance device of claim 1 wherein the capacitor plates comprise aluminum, copper, silver, gold, platinum, or a combination of two or more thereof.

\* \* \* \* \*